United States Patent
Sueta et al.

(10) Patent No.: US 11,726,083 B2
(45) Date of Patent: Aug. 15, 2023

(54) METHOD FOR TESTING DRUG RESPONSE OF CARDIOMYOCYTES

(71) Applicant: Myoridge Co. Ltd., Kyoto (JP)

(72) Inventors: Shinichi Sueta, Kyoto (JP); Itsunari Minami, Kyoto (JP); Tomoko Kasahara, Kyoto (JP); Kentaro Ishida, Kyoto (JP); Naohiro Makita, Kyoto (JP)

(73) Assignee: MYORIDGE CO. LTD., Kyoto (JP)

( * ) Notice: Subject to any disclaimer, the term of this patent is extended or adjusted under 35 U.S.C. 154(b) by 328 days.

(21) Appl. No.: 16/957,625

(22) PCT Filed: Dec. 26, 2018

(86) PCT No.: PCT/JP2018/047956
§ 371 (c)(1),
(2) Date: Jun. 24, 2020

(87) PCT Pub. No.: WO2019/131806
PCT Pub. Date: Jul. 4, 2019

(65) Prior Publication Data
US 2021/0372993 A1  Dec. 2, 2021

(30) Foreign Application Priority Data
Dec. 26, 2017  (JP) ................ 2017-249552

(51) Int. Cl.
C12Q 1/02  (2006.01)
G01N 33/50  (2006.01)
G01N 33/84  (2006.01)

(52) U.S. Cl.
CPC ......... *G01N 33/5061* (2013.01); *G01N 33/84* (2013.01); *G01N 2500/10* (2013.01)

(58) Field of Classification Search
CPC .................................................. C12Q 1/025
See application file for complete search history.

(56) References Cited

FOREIGN PATENT DOCUMENTS

| JP | H11-137241 A | 5/1999 |
| JP | 2013-543726 A | 12/2013 |
| WO | WO 2007/094511 A1 | 8/2007 |
| WO | WO 2011/122200 A1 | 10/2011 |
| WO | WO 2012/032761 A1 | 3/2012 |

(Continued)

OTHER PUBLICATIONS

English machine translation of Hoffman La Roche AG, JP 2013-543726 A, 2013.*

(Continued)

*Primary Examiner* — Rosanne Kosson
(74) *Attorney, Agent, or Firm* — John P. White

(57) ABSTRACT

A method for testing drug response of a cardiomyocyte, the method comprising: testing a response of the cardiomyocyte to an added drug in a culture medium under a condition in which a distance from a liquid surface of the culture medium to a bottom surface of a culture vessel contacted by the cardiomyocyte is 5.0 mm or less; or testing a response of the cardiomyocyte to an added drug immediately after placing the cardiomyocyte in a culture medium under a condition in which a distance from a liquid surface of the culture medium to a bottom surface of a culture vessel contacted by the cardiomyocyte is 5.0 mm or less.

5 Claims, 21 Drawing Sheets

(56) References Cited

FOREIGN PATENT DOCUMENTS

| WO | WO 2012/055828 A1 | 5/2012 |
|---|---|---|
| WO | WO 2012/117688 A1 | 9/2012 |
| WO | WO 2016/121840 A1 | 8/2016 |

OTHER PUBLICATIONS

Place et al., "Limitations of oxygen delivery to cells in culture: an underappreciated problem in basic and translational research," Free Radic Biol Med 113:311-322, published online on Oct. 13, 2017.*
Jacquith, 96-well plate dimensions [standard microplate], https://www.wellplate.com/96-well-plate-dimensions/, 2014.*
Perkin Elmer, Microplate dimensions, working volumes and packaging, https://www.perkinelmer.com/lab-products-and-services/application-support-knowledgebase/microplates/plate-dimensions.html; published online on Aug. 16, 2016.*
Internet Archive Wayback Machine, https://web.archive.org/web/20160901000000*/https://www.perkinelmer.com/lab-products-and-services/application-support-knowledgebase/microplates/plate-dimensions.html, 2016.*
Eppendorf AG, Technical Data Sheet, https://www.eppendorf.com/product-media/doc/en/90656/Eppendorf_Consumables_Technical-data_Cell-Culture-Plate-6-Well.pdf, 2013.*
Extended European Search Report dated Dec. 8, 2021 in connection with European Patent Application No. EP 18897156.
English translation of International Preliminary Report on Patentability dated Jul. 2, 2020 in connection with PCT/JP2018/047956.
Takahiko Suzuki et al., "Effective Oxygen Supply Stimulates the Beating of Cultured Cardiac Myocytes in a Serum-Free Medium", J. Exp. & Appl. Cell Cult. Rsrch, vol. 14., No. 1, p. 61 (1995).
Erina Maeyama et al., "Construction of a new culture technique to achieve efficient oxygen supply", Regenerative Medicine. vol. 13, Suppl., p. 222 (2014).
European search report dated Sep. 3, 2021 in corresponding European Patent Application No. 18897156.8.
Oksana Sirenko et al., (2013) "Assessment of beating parameters in human induced pluripotent stem cells . . . ", Toxicology and Applied Pharmacology, vol. 273, No. 3, pp. 500-507.
Oksana Sirenko et al., Supplemental Figure 1, "Assessment of beating parameters in human . . . ", Toxicology and Applied Pharmacology, vol. 273, No. 3, pp. 500-507, p. 1 (2013).
Takahiko Suzuki et al., (1995) "Effective oxygen Supply Stimulates the Beating of Cultured Cardiac Myocytes in . . . ", J. Exp. & Appl. Cell Cult. Rsrch, vol. 14, No. 1, pp. 39-61.
Rohin K. Iyer et al., (2007) "Synthetic Oxygen Carriers in Cardiac Tissue Engineering", Artificial Cells, Blood Substitutes, and Biotechnology, vol. 35, pp. 135-148.
Milica Radisic et al., (2006) Biomimetic Approach to Cardiac Tissue Engineering: Oxygen Carriers and Channeled Scaffolds, Tissue Engineering, vol. 12, No. 8, pp. 2077-2091.
Daryl E. Powers et al., (2009) "Accurate Control of Oxygen Level in Cells During Culture on Silicone Rubber Membranes . . . ", Biotechnol. Progress, vol. 26, No. 3, pp. 805-818.
Ando, et al., "A new paradigm for drug-induced torsadogenic risk assessment using human iPS cell-derived cardiomyocytes", J. Pharmacol. Toxicol. Methods., Dec. 2016, Vo. 84, pp. 111-127.
Carrier, et al., "Effects of Oxygen on Engineered Cardiac Muscle", Biotechnol. Bioeng., vol. 78, No. 6, pp. 617-625.
International Search Report dated Apr. 2, 2019 in connection with PCT International Application No. PCT/JP2018/047956.
Written Opinion (form PCT/ISA/237) dated Oct. 18, 2019 in connection with PCT International Application No. PCT/JP2018/047956.
WO 2012/032761 A1 (Toyo Seikan Kaisha, Ltd.), published Mar. 15, 2012.
JP H11-137241 A (Otsuka Techno KK; Mitsui Chem Inc), published May 25, 1999.
WO 2007/094511 A1 (Oxygenix Co Ltd; Univ Tokyo), published Aug. 23, 2007.
WO 2016/121840 A1 (Univ Tokyo; Somar Corp), published Aug. 4, 2016.
Cosmo Bio News, Cosmo Bio Co., Ltd., Mar. 2017, No. 127, p. 170.
Cosmo Bio News, Cosmo Bio Co., Ltd., Apr. 2016, No. 116, p. 20.
Japanese offical action dated May 9, 2023 in corresponding Japanese Patent Application No. 2019-562130.
Japanese official action dated May 9, 2023 in corresponding Japanese Patent Application No. 2019-562130.
Cosmo Bio News, Cosmo Bio Co., Ltd., Mar. 2017, No. 127, p. 17.

* cited by examiner

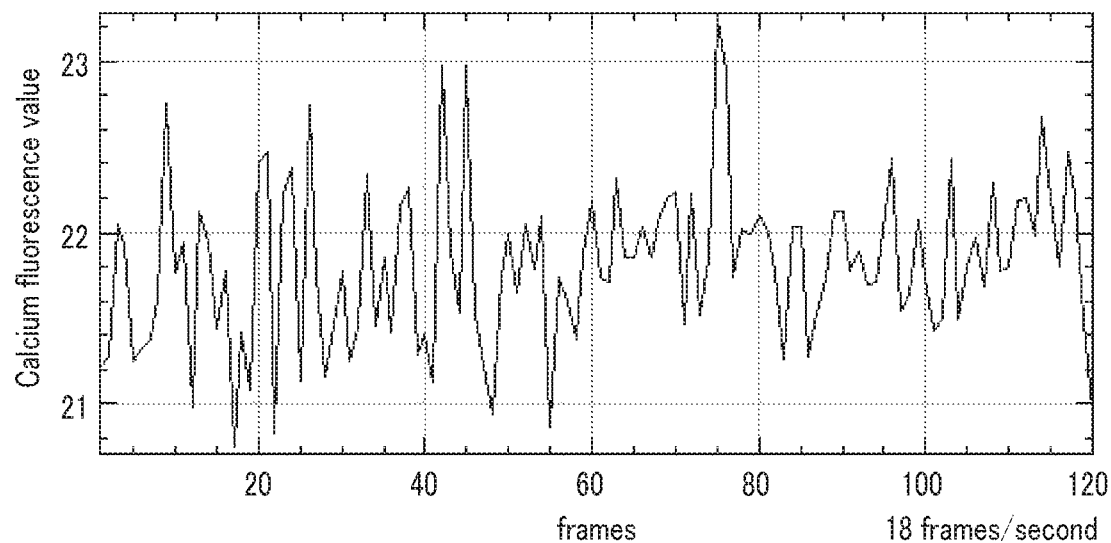
F I G. 12A
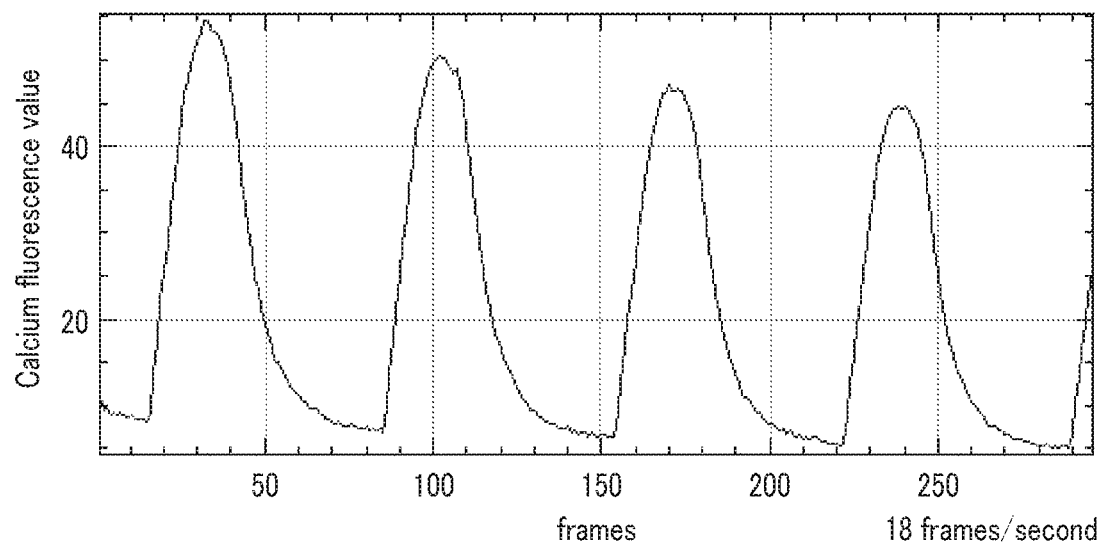
F I G. 12B

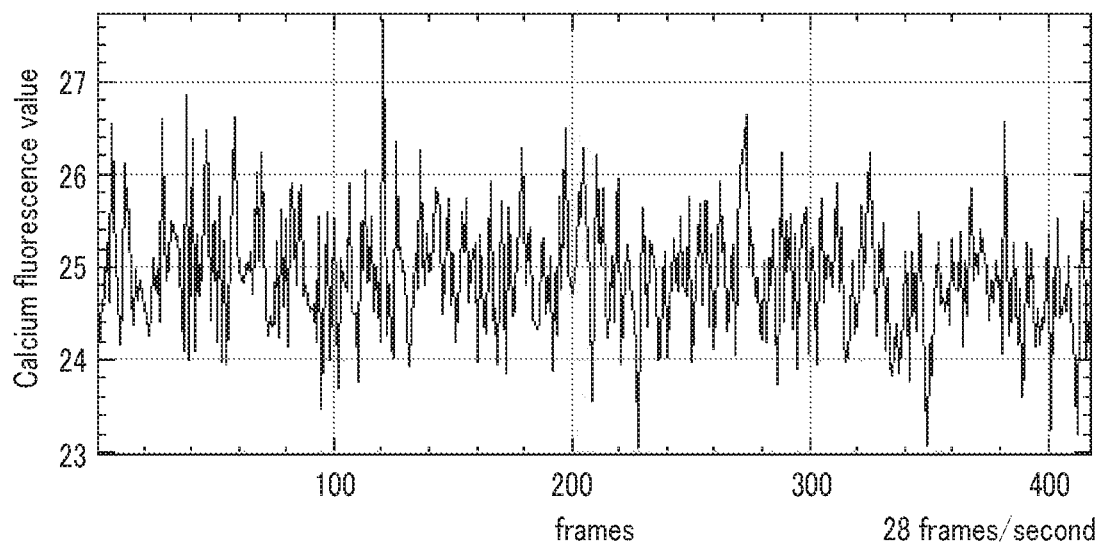
F I G. 14A
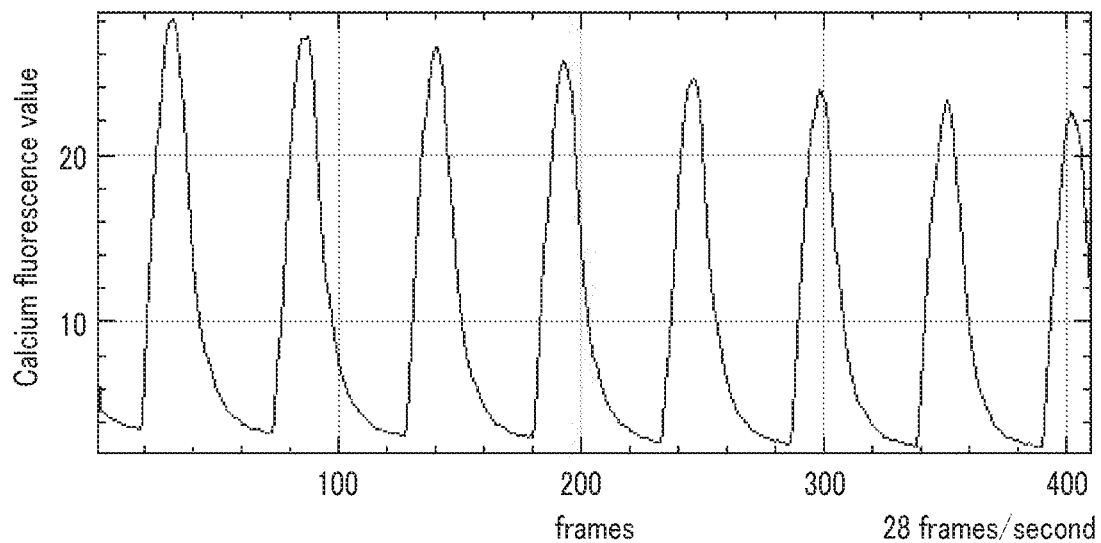
F I G. 14B

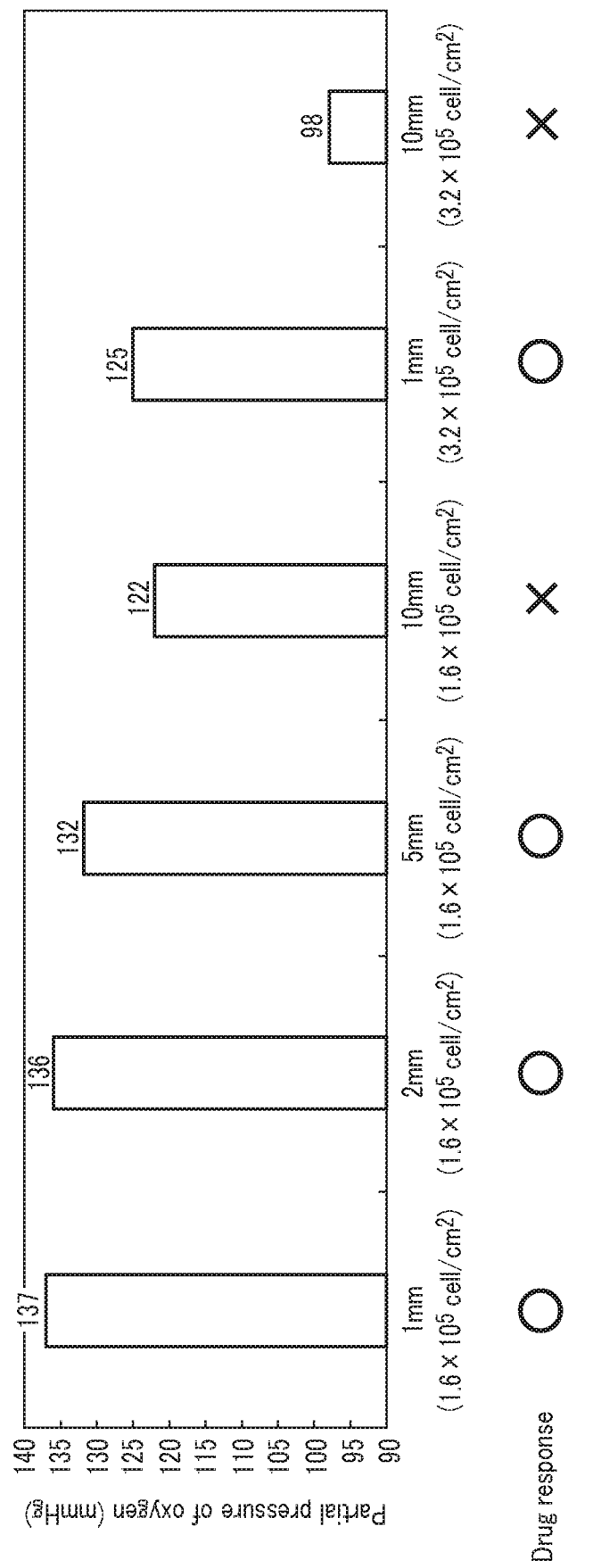
F I G. 18

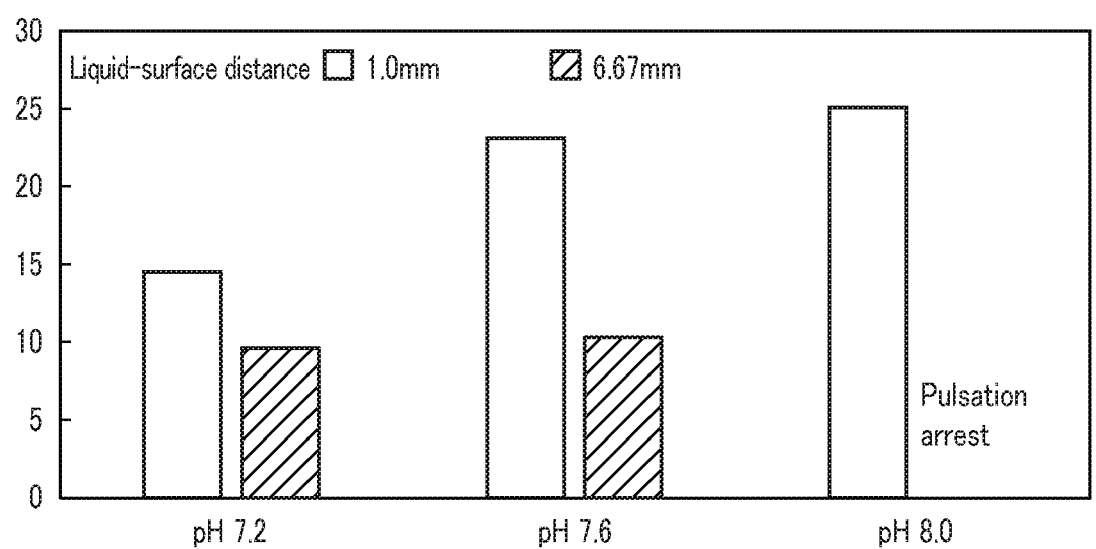
F I G. 19

METHOD FOR TESTING DRUG RESPONSE OF CARDIOMYOCYTES

CROSS-REFERENCE TO RELATED APPLICATIONS

This is a U.S. national phase application under 35 USC § 371 of International Application PCT/JP2018/047956 (not published in English), filed Dec. 26, 2018, claiming priority of Japanese Patent Application No. 2017-249552, filed Dec. 26, 2017, the contents of each of which are hereby incorporated by reference into the application.

FIELD

The present invention relates to a method for testing drug response of cardiomyocytes.

BACKGROUND

Nowadays, it is said that the development of new drugs takes at least ten years and costs several tens of billions of yen, and it is expected that especially preclinical testing such as animal testing, which is costly and time consuming, will be replaced by testing that uses in-vitro cultured cells or will be conducted more efficiently. Also, it is considered possible to evaluate the medicinal efficacy of a drug candidate substance by using in-vitro cultured cells and to perform high-throughput screening (drug discovery screening).

The heart is an organ that is directly linked to life, and there is an overwhelmingly large number of patients with heart disease in developed countries. Also, every drug that we take requires close attention to the side effects on the heart (safety pharmacology). In order to accelerate preclinical testing such as animal testing in the development of new drugs, a method for evaluating drug response and a method for evaluating cardiotoxicity are being developed using human cardiomyocytes prepared from iPS cells.

Many cases have been reported in which cardiomyocytes prepared by inducing differentiation of iPS cells are used to evaluate drug response (e.g., Non-patent Literature 1: J Pharmacol Toxicol Methods. 2017 March-April; 84: 111-127. doi: 10.1016/j.vascn.2016.12.003. Epub 2016 Dec. 10.). Non-patent Literature 1 discloses that cardiomyocytes prepared by inducing differentiation of iPS cells are treated with a trypsin solution, then seeded in a culture medium for cardiomyocytes, and cultured to produce a beating cardiomyocyte sheet, to which a drug is added in a certain concentration range to measure the electrophysiological changes of the cardiomyocytes by extracellular potential recording.

CITATION LIST

Non Patent Literature

Non-Patent Literature 1:
J Pharmacol Toxicol Methods. 2017 March-April; 84: 111-127. doi: 10.1016/j.vascn.2016.12.003. Epub 2016 Dec. 10.

SUMMARY

Technical Problem

When the inventors of the present invention evaluated drug response using cardiomyocytes prepared by inducing differentiation of iPS cells, the inventors found a problem that there were cases where the cardiomyocytes could not properly exhibit a drug-response effect, such as the pulsation of the cardiomyocytes stopping during the evaluation, the cardiomyocytes failing to show an expected drug response (e.g., tachycardic response, arrhythmic response caused by early afterdepolarization (EAD)), and the like. Accordingly, it is an object of the present invention to provide a technique for solving the newly-found problem, that is, to provide a technique for testing drug response of cardiomyocytes that enables cardiomyocytes to properly exhibit a drug-response effect.

Solution to Problem

According to a first embodiment, there is provided a method for testing drug response of a cardiomyocyte, the method comprising:
testing a response of the cardiomyocyte to an added drug in a culture medium containing an oxygen carrier; or
testing a response of the cardiomyocyte to an added drug immediately after placing the cardiomyocyte in a culture medium containing an oxygen carrier.

According to a second embodiment, there is provided a method for testing drug response of a cardiomyocyte, the method comprising:
testing a response of the cardiomyocyte to an added drug in a culture medium under a condition in which a distance from a liquid surface of the culture medium to a bottom surface of a culture vessel contacted by the cardiomyocyte is 5.0 mm or less; or
testing a response of the cardiomyocyte to an added drug immediately after placing the cardiomyocyte in a culture medium under a condition in which a distance from a liquid surface of the culture medium to a bottom surface of a culture vessel contacted by the cardiomyocyte is 5.0 mm or less.

According to a third embodiment, there is provided a method for testing drug response of a cardiomyocyte, the method comprising:
testing a response of the cardiomyocyte to an added drug in a culture medium contained in a container having an oxygen permeability; or
testing a response of the cardiomyocyte to an added drug immediately after placing the cardiomyocyte in a culture medium contained in a container having an oxygen permeability.

According to a fourth embodiment, there is provided a method for testing drug response of a cardiomyocyte, the method comprising:
testing a response of the cardiomyocyte to an added drug in a culture medium under a measure to increase a rate of oxygen supply to the cardiomyocyte; or
testing a response of the cardiomyocyte to an added drug immediately after placing the cardiomyocyte in a culture medium under a measure to increase a rate of oxygen supply to the cardiomyocyte.

According to a fifth embodiment, there is provided a method for testing drug response of a cardiomyocyte, the method comprising:
testing a response of the cardiomyocyte to an added drug under a condition in which a cardiomyocyte-containing culture medium is maintained to have a partial pressure of oxygen of 125 mmHg or more in the absence of a drug; or
testing a response of the cardiomyocyte to an added drug immediately after placing the cardiomyocyte under a condition in which a cardiomyocyte-containing culture medium is maintained to have a partial pressure of oxygen of 125 mmHg or more in the absence of a drug.

According to other embodiments, there is provided a method for testing drug response of a cardiomyocyte, the method comprising:

a) testing a response of the cardiomyocyte to an added drug in a culture medium placed under a high oxygen concentration atmosphere, or testing a response of the cardiomyocyte to an added drug immediately after placing the cardiomyocyte in a culture medium placed under a high oxygen concentration atmosphere;

b) testing a response of the cardiomyocyte to an added drug in a culture medium while bubbling an oxygen-containing gas into the culture medium, or testing a response of the cardiomyocyte to an added drug immediately after placing the cardiomyocyte in a culture medium into which an oxygen-containing gas is being bubbled;

c) testing a response of the cardiomyocyte to an added drug in a culture medium while shaking the culture medium, or testing a response of the cardiomyocyte to an added drug immediately after placing the cardiomyocyte in a shaking culture medium; or d) testing a response of the cardiomyocyte to an added drug in a culture medium having a high amount of dissolved oxygen in a circulation-type culture system that supplies the culture medium, or testing a response of the cardiomyocyte to an added drug immediately after placing the cardiomyocyte in a culture medium having a high amount of dissolved oxygen in a circulation-type culture system that supplies the culture medium.

According to another aspect, there is provided an agent for inhibiting a pulsation arrest of a cardiomyocyte, comprising an oxygen carrier; or an agent for enhancing drug response of a cardiomyocyte, comprising an oxygen carrier.

According to still another aspect, there is provided a kit for drug response testing, comprising a culture medium for cardiomyocytes, and an oxygen carrier.

According to still another aspect, there is provided a culture medium for drug response testing, comprising a culture medium for cardiomyocytes, and an oxygen carrier.

Advantageous Effects of Invention

According to the present invention, it is possible to provide a technique for testing drug response of cardiomyocytes that enables cardiomyocytes to properly exhibit a drug-response effect.

BRIEF DESCRIPTION OF THE DRAWINGS

FIG. 12A is a waveform diagram of a sample 5K after addition of a drug.

FIG. 12B is a waveform diagram of a sample 5L before addition of a drug.

FIG. 14A is a waveform diagram of a sample 5O after addition of a drug.

FIG. 14B is a waveform diagram of a sample 5P before addition of a drug.

FIG. 18 is a diagram showing results of measurement of partial pressure of oxygen and results of drug response testing.

FIG. 19 is a graph showing response of cardiomyocytes to changes in pH of a culture medium.

DETAILED DESCRIPTION

Figure 1:
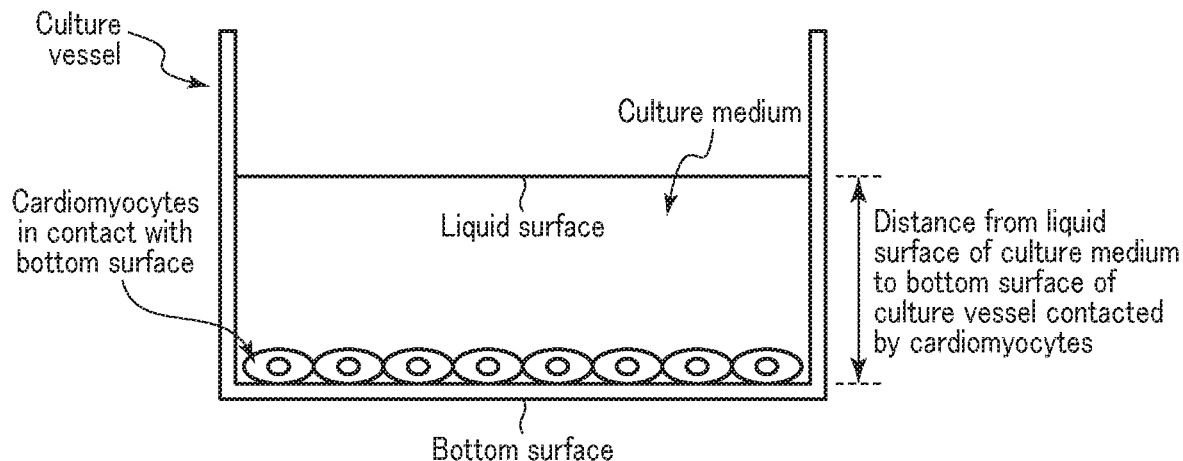
FIG. 1 is a schematic diagram illustrating "a distance from a liquid surface of a culture medium to a bottom surface of a culture vessel contacted by cardiomyocytes".

The inventors of the present invention evaluated drug response using cardiomyocytes prepared by inducing differentiation of iPS cells, and found a problem that an expected drug response was detected only within a range of drug concentration that is more limited than expected when drugs known to have a pharmacological effect on the heart were added (see Example 1 below). As a result of conducting intensive research to solve this problem, the inventors of the present invention discovered that adopting a configuration for increasing the amount of oxygen supplied to the cardiomyocytes would solve the problem, and completed the present invention.

The present invention will be described below. The description provided below is intended to illustrate the present invention, and not intended to limit the present invention.

1. Method for Testing Drug Response 1-1. First Embodiment

According to a first embodiment, a method for testing drug response of a cardiomyocyte includes:

testing a response of the cardiomyocyte to an added drug in a culture medium containing an oxygen carrier; or testing a response of the cardiomyocyte to an added drug immediately after placing the cardiomyocyte in a culture medium containing an oxygen carrier.

In the first embodiment, the cardiomyocyte may be tested in a culture medium containing an oxygen carrier or tested immediately after the cardiomyocyte is placed in a culture medium containing an oxygen carrier. The former literally means that the testing is conducted in a culture medium containing an oxygen carrier. The latter means that the testing may be conducted either in a culture medium not containing an oxygen carrier or in a culture medium containing an oxygen carrier, immediately after the cardiomyocyte is placed in a culture medium containing an oxygen carrier.

In the latter case, the phrase "immediately after" typically refers to within two hours, preferably within one hour, and more preferably within 30 minutes. Also, in the latter case, the period in which the cardiomyocyte is placed under a predetermined condition prior to the testing (in the present embodiment, the period in which the cardiomyocyte is placed in a culture medium containing an oxygen carrier prior to the testing) is a period needed to supply a sufficient amount of oxygen to the cardiomyocyte in advance, and may be, for example, one or more minutes, preferably 10 or more minutes. The upper limit of said period may be, for example, 120 minutes. However, since the cardiomyocyte can be cultured for a long period of time, the upper limit of said period is not particularly limited, and the cardiomyocyte may be cultured or stored in a culture medium containing an oxygen carrier for a long period of time prior to the testing.

The cardiomyocyte may be a cardiomyocyte prepared by inducing differentiation of a pluripotent stem cell or a primary cultured cardiomyocyte isolated from the heart of an organism. The cardiomyocyte may also be a commercially available cardiomyocyte derived from a pluripotent stem cell (e.g., iCell of CDI, MiraCell of Takara Bio Inc., Cor.4U of Axiogenesis, etc.). The "pluripotent stem cell" refers to a cell having pluripotency, which is an ability to differentiate into any type of cell constituting an adult body, and a self-replication capability, which is an ability to maintain the pluripotency even after cell division. The "pluripotent stem cell" includes an embryonic stem cell (an ES cell), an embryonic germ cell (an EG cell), and an induced pluripotent stem cell (an iPS cell). The cardiomyocyte is preferably a cardiomyocyte prepared by inducing differentiation of an iPS cell (hereinafter also referred to as an "iPS cell-derived cardiomyocyte"). The iPS cell-derived cardiomyocyte can be prepared by a known method for inducing myocardial differentiation such as a method for inducing protein-free cardiac differentiation (PFCD) (see WO2015/182765).

The cardiomyocyte may be a cardiomyocyte of any organism; however, it is preferably a mammalian cardiomyocyte, and more preferably a human cardiomyocyte.

The cardiomyocyte may be a normal cardiomyocyte, a cardiomyocyte with a genetic mutation, or a disease model cardiomyocyte. Alternatively, the cardiomyocyte may be a cardiomyocyte derived from a subject whose response to a drug is desired to be examined. The normal cardiomyocyte may be a cardiomyocyte derived from a normal subject (i.e., a subject without hereditary heart disease) or a commercially available cardiomyocyte. The cardiomyocyte with a genetic mutation may be a cardiomyocyte derived from a subject with a genetic mutation or a cardiomyocyte obtained by introducing a genetic mutation into a normal cardiomyocyte. The disease model cardiomyocyte may be a cardiomyocyte derived from a subject with hereditary heart disease or a cardiomyocyte obtained by introducing a gene causing hereditary heart disease into a normal cardiomyocyte.

Accordingly, the cardiomyocyte is preferably a cardiomyocyte derived from a human iPS cell, and the cardiomyocyte derived from a human iPS cell includes a normal cardiomyocyte and a disease model cardiomyocyte. More preferably, the cardiomyocyte is a mature cardiomyocyte derived from a human iPS cell, and the mature cardiomyocyte derived from a human iPS cell includes a normal mature cardiomyocyte and a mature cardiomyocyte of a disease model.

The term "mature cardiomyocyte derived from a human iPS cell" is used in contrast with the term "immature cardiomyocyte derived from a human iPS cell" in the pertinent technical field, and the mature cardiomyocyte derived from a human iPS cell has a higher ion channel function than the immature cardiomyocyte derived from a human iPS cell.

The "mature cardiomyocyte derived from a human iPS cell" is, for example, a cell in a state where 14 or more days have passed since the induction of differentiation of an iPS cell was initiated. The day when the induction of differentiation of an iPS cell is initiated is the day when an iPS cell maintained in an undifferentiated state is subjected to treatment for transferring to a differentiated state, and is set to be Day 0. Since the mature cardiomyocyte can be cultured for a long period of time while maintaining the differentiated state, the upper limit of the number of days since initiation of the induction of differentiation is not particularly limited, and the mature cardiomyocyte may be cultured or stored for a long period of time while maintaining the differentiated state. For example, the mature cardiomyocyte may be a cell in a state where 365 or more days have passed since the induction of differentiation of an iPS cell was initiated. Preferably, the "mature cardiomyocyte derived from a human iPS cell" refers to a cell in a state where 14 or more days have passed since the induction of differentiation of an iPS cell was initiated by the method for inducing protein-free cardiac differentiation (PFCD).

Since the "mature cardiomyocyte derived from a human iPS cell" has a higher oxygen demand than the immature cardiomyocyte derived from a human iPS cell, the effect of the present invention can be more remarkably exhibited.

The cardiomyocyte may be tested in the form of a single cell; however, it is preferably tested in the form of a cardiomyocyte sheet made of multiple cardiomyocytes bonded to each other, as described in the Examples below, or in the form of a cardiomyocyte mass.

In the first embodiment, a culture medium containing an oxygen carrier is used.

The oxygen carrier is a substance having a function of carrying oxygen to cells, preferably a substance having a property of binding to oxygen under a high oxygen concentration and separating oxygen under a low oxygen concentration. The oxygen carrier is, for example, a red blood cell, an oxygen-carrying protein, or an artificial oxygen carrier, and is preferably an oxygen-carrying protein. Examples of the oxygen-carrying protein include hemoglobin, modified hemoglobin (e.g., HemoAct, which is a hemoglobin-albumin complex; see WO2012/117688), myoglobin, hemerythrin, hemocyanin, erythrocruorin, pinnaglobin, vanabins, leghemoglobin, chlorocruorin, or variants thereof. Examples of the artificial oxygen carrier include a nanocapsule-type oxygen carrier, an artificial red blood cell, and Hb endoplasmic reticulum. Examples of the red blood cell include a red blood cell prepared from human blood or mammalian blood. Chemical substances having a function of carrying oxygen to cells, such as perfluorinated compounds (perfluorochemicals), are also included in the oxygen carrier.

The concentration of the oxygen carrier in the culture medium is not particularly limited; however, the oxygen carrier is preferably contained in the culture medium at a concentration sufficient to perform the function of carrying oxygen to cells. For example, if the oxygen carrier is an oxygen-carrying protein such as hemoglobin, the oxygen-carrying protein is contained in the culture medium in an amount of preferably 0.1 to 10% by mass, more preferably 0.5 to 5.0% by mass, and still more preferably 2.0 to 5.0% by mass, with respect to the culture medium.

The culture medium for adding an oxygen carrier may be a known culture medium for culturing cardiomyocytes or a known culture medium for measuring the potential of cardiomyocytes. Preferably, the culture medium for adding an oxygen carrier contains inorganic salts including calcium salt, magnesium salt, potassium salt, and sodium salt, and a buffer solution. More preferably, a basal medium such as DMEM, RPMI, IMDM, Ham-12 or the like may be used as the culture medium for adding an oxygen carrier. The basal medium is available from, for example, Sigma-Aldrich Japan. Alternatively, a culture medium having the following composition may be used as the culture medium for adding an oxygen carrier:

0.01 to 0.5 g/L (e.g., 0.182 g/L) of $CaCl_2$,
0 to 1.0 g/L (e.g., 0.09767 g/L) of $MgSO_4$,
0.1 to 1.0 g/L (e.g., 0.4 g/L) of KCl,
0 to 10.0 g/L (e.g., 3.362 g/L) of $NaHCO_3$,
1.0 to 20.0 g/L (e.g., 5.4525 g/L) of NaCl,
0 to 1.0 g/L (e.g., 0.109 g/L) of $Na_2HPO_4$, and
0 to 20.0 g/L (e.g., 5.958 g/L) of HEPES.

The culture medium having the above composition may contain no serum, or contain a serum in an amount of 40% by mass or less with respect to the culture medium. The pH of the culture medium for adding an oxygen carrier is not particularly limited; however, it is preferably from 6.0 to 9.0, and more preferably from 7.0 to 8.0.

Any container used for adhesion culture of cells may be used as the culture vessel. In general, a flat-bottomed container, such as a culture dish or a microtiter plate, can be used as the culture vessel. More specifically, a cell culture dish having a diameter of 3.5 to 10 cm, a 6-well plate, a 12-well plate, a 24-well plate, a 96-well plate, a 384-well plate, a cell culture bag, or the like may be used as the culture vessel.

As described in the Examples below, when a 96-well plate is used, cardiomyocytes are seeded at, for example, about $2 \times 10^4$ to about $8 \times 10^4$ cells/well and cultured in a culture medium to produce a cardiomyocyte sheet, which can be used for drug response testing. That is, cardiomyocytes are seeded in the culture vessel at, for example, about $0.625 \times 10^5$ to about $2.5 \times 10^5$ cells/cm² and cultured in a culture medium to produce a cardiomyocyte sheet, which can be used for drug response testing.

The drug response testing may be performed by adding a drug to a culture medium containing cardiomyocytes and analyzing the pulsation of the cardiomyocytes by a known method. For example, the drug response testing may be performed using an apparatus capable of conducting an electrophysiological analysis of cells and/or a motion analysis of cells. More specifically, the drug response testing may be performed by, for example, a calcium imaging method using a fluorescence microscope, a pulsation analysis using a motion analyzer, an extracellular potential analysis using a multi-electrode system, an MEA (multi-electrode array) analysis, or an intracellular potential analysis using a whole-cell patch clamp.

The drug used in the drug response testing may be a substance known to have effects on cardiomyocytes, such as isoproterenol (ISO), verapamil, E-4031, terfenadine, astemizole, chromanol 293b, mexiletine, nifedipine, propranolol, milrinone, the drugs described in the literature (J Pharmacol Toxicol Methods. 2017 March-April; 84: 111-127. doi: 10.1016/j.vascn.2016.12.003. Epub 2016 Dec. 10) cited in the Background, or the like. ISO is a non-selective β-agonist and has a tachycardic effect and a cardiotonic effect. Milrinone is a phosphodiesterase III inhibitor and likewise has a tachycardic effect and a cardiotonic effect. Verapamil is an L-type calcium channel inhibitor. E-4031 is an hERG-type potassium channel inhibitor. Terfenadine is an anti-allergenic drug and is known to cause QT prolongation. Astemizole is an anti-allergenic drug and is known to cause QT prolongation. Chromanol 293b is a voltage-dependent potassium channel KCNQ1 inhibitor. Mexiletine is a voltage-dependent sodium channel inhibitor. Nifedipine is an L-type calcium channel inhibitor. Propranolol is a β-blocker and has a bradycardic effect.

Alternatively, the drug may be a substance whose effects on cardiomyocytes are desired to be examined, and is, for example, a candidate substance for a new drug, a substance suspected to have cardiotoxicity, or a candidate substance that causes drug response of cardiomyocytes. The candidate substance that causes drug response of cardiomyocytes may be, for example, a candidate substance that causes drug response selected from the group consisting of drug-induced QT prolongation response, bradycardic response (negative chronotropic effect), tachycardic response (positive chronotropic effect), cardiotonic response (positive inotropic effect), cardiac weakening response (negative inotropic effect), early afterdepolarization (EAD) response, delayed afterdepolarization (DAD) response, torsades de pointes (TdP) response, triggered activity arrhythmia response, and re-entry arrhythmia response. The drug may be a low-molecular compound included in small molecule drugs, or a high-molecular compound, such as a protein, an antibody, a nucleic acid, a polysaccharide or the like, that is included in macromolecular drugs.

The concentration of the drug added can be suitably selected according to the known art depending on the type of the drug, and, for example, the literature (J Pharmacol Toxicol Methods. 2017 March-April; 84: 111-127. doi: 10.1016/j.vascn.2016.12.003. Epub 2016 Dec. 10) cited in the Background can be referred to. As is apparent from the cited literature and the common technical knowledge, although the concentration of the drug added differs depending on the type of the drug, the drug may be added to the culture medium at a concentration of, for example, 0.00001 to 10000 μM.

For example, when a substance known to have effects on cardiomyocytes is used as the drug and a cardiomyocyte derived from a subject whose response to the drug is desired to be examined is used as the cardiomyocyte, the effects of the drug on the cardiomyocyte of the subject can be examined. Alternatively, when a substance whose effects on cardiomyocytes are desired to be examined is used as the drug and a normal cardiomyocyte is used as the cardiomyocyte, the effects of the drug on the normal cardiomyocyte can be examined. Alternatively, when a substance whose effects on cardiomyocytes are desired to be examined is used as the drug and the above-described disease model cardiomyocyte is used as the cardiomyocyte, the effects of the drug on the cardiomyocyte of a subject with a hereditary disease can be examined.

More specifically, the method of the present invention can be used to evaluate the safety and effectiveness of drugs in the drug discovery process. That is, the cardiotoxicity of a candidate substance for a new drug can be evaluated by using the candidate substance for a new drug as the drug and using a normal cardiomyocyte as the cardiomyocyte. Also, by using a candidate substance for a new drug as the drug and using a disease model cardiomyocyte as the cardiomyocyte, a compound effective for the treatment of the disease can be found.

In the first embodiment, the culture medium containing an oxygen carrier is used in the drug response testing; thereby, the effects described below can be achieved. That is, it is possible to suppress the occurrence of an arrest of the pulsation of the cardiomyocyte during the drug response testing (see Examples 2 and 5 below). It is also possible to extend the range of the drug concentration that can be applied in the drug response testing (see Examples 2 and 5 below). Furthermore, it is possible to detect the change in the waveform caused by the addition of the drug (e.g., prolongation of the duration of the action potential waveform or the $Ca^{2+}$ waveform, which corresponds to QT prolongation, arrhythmia due to early afterdepolarization (EAD), or the like) as a more distinct change in the waveform (see Example 6 below).

It is considered that since an oxygen carrier is contained in the culture medium in the first embodiment, the rate of oxygen supply to the cardiomyocyte is increased, allowing the cardiomyocyte to properly exhibit the drug-response effect.

It is not known exactly why the present invention can achieve the above effects; however, according to the studies conducted by the inventors of the present invention, the following may be one possible reason: during the drug response testing, the oxygen demand of the cardiomyocyte increases due to an increase in the number of pulsations, activation of muscle contraction, activation of an intracellular signal transduction system or an ion pump, consumption of ATP caused thereby, or some other reasons, and thus the amount of oxygen in the culture medium becomes insufficient, resulting in an arrest of the pulsation or an inability to exhibit the expected drug effect (such as tachycardic response or arrhythmic response caused by EAD); and it is considered that such a phenomenon can be suppressed by adopting the configuration for increasing the amount of oxygen supplied to the cardiomyocyte according to the present invention.

1-2. Second Embodiment

According to a second embodiment, a method for testing drug response of a cardiomyocyte includes:

testing a response of the cardiomyocyte to an added drug in a culture medium under a condition in which a distance from a liquid surface of the culture medium to a bottom surface of a culture vessel contacted by the cardiomyocyte is 5.0 mm or less; or testing a response of the cardiomyocyte to an added drug immediately after placing the cardiomyocyte in a culture medium under a condition in which a distance from a liquid surface of the culture medium to a bottom surface of a culture vessel contacted by the cardiomyocyte is 5.0 mm or less.

Hereinafter, only the portions different from the first embodiment will be described, and descriptions of the portions overlapping with the first embodiment will be omitted. That is, whereas the "culture medium containing an oxygen carrier" is used in the drug response testing in the first embodiment, the "condition in which a distance from a liquid surface of the culture medium to a bottom surface of a culture vessel contacted by the cardiomyocyte (hereinafter also referred to a "liquid-surface distance") is 5.0 mm or less" is adopted in the second embodiment. Therefore, only said condition will be described below.

In the second embodiment, the cardiomyocyte may be tested under the condition in which the liquid-surface distance is 5.0 mm or less, or tested immediately after the cardiomyocyte is placed under the condition in which the liquid-surface distance is 5.0 mm or less. The former literally means that the testing is conducted under the condition in which the liquid-surface distance is 5.0 mm or less. The latter means that the testing may be conducted either under a condition that does not satisfy the above-described condition in which the liquid-surface distance is 5.0 mm or less or under the above-described condition in which the liquid-surface distance is 5.0 mm or less, immediately after the cardiomyocyte is placed under the condition in which the liquid-surface distance is 5.0 mm or less.

As noted above, "immediately after" typically refers to within two hours, preferably within one hour, and more preferably within 30 minutes. Also, as noted above, the period in which the cardiomyocyte is placed under a predetermined condition prior to the testing (in this embodiment, the period in which the cardiomyocyte is placed under the condition in which the liquid-surface distance is 5.0 mm or less prior to the testing) may be, for example, one or more minutes, preferably 10 or more minutes. The upper limit of said period may be, for example, 120 minutes. However, since the cardiomyocyte can be cultured for a long period of time, the upper limit of said period is not particularly limited, and the cardiomyocyte may be cultured or stored for a long period of time under the condition in which the liquid-surface distance is 5.0 mm or less prior to the testing.

In the embodiments described below as well, the same expression "testing a response of the cardiomyocyte to an added drug . . . immediately after placing the cardiomyocyte . . . " is used. This expression has the same meaning as the above description; thus, the above description can be referred to.

The "distance from a liquid surface of the culture medium to a bottom surface of a culture vessel contacted by the cardiomyocyte (that is, the liquid-surface distance)" refers to the distance shown in FIG. 1. The "bottom surface of a culture vessel" refers to an inner bottom surface of a culture vessel. As described above, the culture vessel is a container used for adhesion culture of cells and is generally a flat-bottomed container such as a culture dish or a microtiter plate. FIG. 1 shows a flat-bottomed container; however, the culture vessel may be a V-bottomed container. In this case, the liquid-surface distance refers to a "distance from the liquid surface of the culture medium to the deepest part of the bottom surface of the culture vessel contacted by the cardiomyocyte".

The liquid-surface distance is 5.0 mm or less, preferably 3.5 mm or less, more preferably 1.5 mm or less, and still more preferably 1.0 mm or less. The lower limit of the liquid-surface distance is, for example, 0.1 mm. The liquid-surface distance can be varied by changing the amount of the culture medium.

In the second embodiment, the drug response testing can be performed in the same manner as in the first embodiment except that the condition in which the liquid-surface distance is 5.0 mm or less is adopted.

In the second embodiment, the condition in which the liquid-surface distance is 5.0 mm or less is adopted in the drug response testing; thereby, the effects described below can be achieved as in the first embodiment. That is, it is possible to suppress the occurrence of an arrest of the pulsation of the cardiomyocyte during, the drug response testing (see Examples 3 and 5 below). It is also possible to extend the range of the drug concentration that can be applied in the drug response testing (see Examples 3 and 5 below). Furthermore, it is possible to detect the change in the waveform caused by the addition of the drug (e.g., prolongation of the duration of the action potential waveform or the $Ca^{2+}$ waveform, which corresponds to QT prolongation, arrhythmia due to EAD, or the like) as a more distinct change in the waveform (see Example 6 below).

It is considered that since the liquid-surface distance is shortened in the second embodiment, the distance between the cardiomyocyte in contact with the bottom surface of the culture vessel and the atmosphere becomes short, and the rate of oxygen supply to the cardiomyocyte is increased, allowing the cardiomyocyte to properly exhibit the drug-response effect.

In the second embodiment, when the cell density of cardiomyocytes is equal to or greater than $2.5 \times 10^5$ cells/cm$^2$, the liquid-surface distance is preferably 1.5 mm or less. In the second embodiment, when the cell density of cardiomyocytes is equal to or greater than $1.25 \times 10^5$ cells/cm$^2$, and less than $2.5 \times 10^5$ cells/cm$^2$, the liquid-surface distance is preferably 3.5 mm or less. In the second embodiment, when the cell density of cardiomyocytes is equal to or greater than $0.625 \times 10^5$ cells/cm$^2$, and less than $1.25 \times 10^5$ cells/cm$^2$, the liquid-surface distance is preferably 5.0 mm or less.

1-3. Combination of First Embodiment and Second Embodiment

The first embodiment and the second embodiment may be combined when implemented. That is, according to the combined embodiment, there is provided a method for testing drug response of a cardiomyocyte, the method including:

testing a response of the cardiomyocyte to an added drug in a culture medium containing an oxygen carrier under a condition in which a distance from a liquid surface of the culture medium to a bottom surface of a culture vessel contacted by the cardiomyocyte is 5.0 mm or less; or testing a response of the cardiomyocyte to an added drug immediately after placing the cardiomyocyte in a culture medium containing an oxygen carrier under a condition in which a distance from a liquid surface of the culture medium to a bottom surface of a culture vessel contacted by the cardiomyocyte is 5.0 mm or less.

According to the above combined embodiment, the effects of the invention described in the first embodiment and the second embodiment can be more reliably exhibited (see Examples 5 and 6 below).

1-4. Third Embodiment

According to a third embodiment, there is provided a method for testing drug response of a cardiomyocyte, the method including:

testing a response of the cardiomyocyte to an added drug in a culture medium contained in a container having an oxygen permeability; or testing a response of the cardiomyocyte to an added drug immediately after placing the cardiomyocyte in a culture medium contained in a container having an oxygen permeability.

Hereinafter, only the portions different from the first embodiment will be described, and descriptions of the portions overlapping with the first embodiment will be omitted. That is, whereas the "culture medium containing an oxygen carrier" is used in the drug response testing in the first embodiment, the "container having an oxygen permeability" is used in the third embodiment. Therefore, only said container is described below.

The "container having an oxygen permeability" is specifically a container including a material having a higher oxygen permeability than a container made of a plastic material that is normally used in cell cultures, and is more specifically a container including a material having an oxygen permeability of 750 ml-mm/m2-day-atm or more, and preferably a container including a material having an oxygen permeability of 750 to 50000 ml-mm/m2-day-atm. The "container having an oxygen permeability" is, for example, a container having a gas-permeable film on its bottom surface, examples of which include a VECELL plate (Vessel Inc.) and G-Rex Cell Culture Devices (Argos Technologies, Inc.). The "container having an oxygen permeability" does not include containers made of only a material having a low oxygen permeability, such as plastic.

In the third embodiment, the container having an oxygen permeability is used in the drug response testing; thereby, the effects described below can be achieved as in the first embodiment. That is, it is possible to suppress the occurrence of an arrest of the pulsation of the cardiomyocyte during the drug response testing (see Example 4 below). It is also possible to extend the range of the drug concentration that can be applied in the drug response testing (see Example 4 below).

It is considered that since the container having an oxygen permeability is used in the third embodiment, the rate of oxygen supply to the cardiomyocyte is increased, allowing the cardiomyocyte to properly exhibit the drug-response effect.

1-5. Fourth Embodiment

It is considered that the effects of the present invention are achieved in the first to third embodiments because the rate of oxygen supply to the cardiomyocyte is increased. Accordingly, it is considered that the above-described effects of the present invention can be achieved not only by way of the configurations described in the above embodiments but also by performing drug response testing under "a measure to increase a rate of oxygen supply to the cardiomyocyte".

Therefore, according to a fourth embodiment, there is provided a method for testing drug response of a cardiomyocyte, the method including:

testing a response of the cardiomyocyte to an added drug in a culture medium under a measure to increase a rate of oxygen supply to the cardiomyocyte; or testing a response of the cardiomyocyte to an added drug immediately after placing the cardiomyocyte in a culture medium under a measure to increase a rate of oxygen supply to the cardiomyocyte.

The "measure to increase a rate of oxygen supply to the cardiomyocyte" refers to any measure that can increase the rate of oxygen supply to the cardiomyocyte when the measure is used, as compared to the cases where the measure is not used.

1-6. Fifth Embodiment

According to a fifth embodiment, there is provided a method for testing drug response of a cardiomyocyte, the method including:

testing a response of the cardiomyocyte to an added drug under a condition in which a cardiomyocyte-containing culture medium is maintained to have a partial pressure of oxygen of 125 mmHg or more in the absence of a drug; or testing a response of the cardiomyocyte to an added drug immediately after placing the cardiomyocyte under a condition in which a cardiomyocyte-containing culture medium is maintained to have a partial pressure of oxygen of 125 mmHg or more in the absence of a drug.

Hereinafter, only the portions different from the first embodiment will be described, and descriptions of the portions overlapping with the first embodiment will be omitted. That is, whereas the "culture medium containing an oxygen carrier" is used in the drug response testing in the first embodiment, the "condition in which a cardiomyocyte-containing culture medium is maintained to have a partial pressure of oxygen of 125 mmHg or more in the absence of a drug (hereinafter also referred to as a "high oxygen partial pressure condition")" is used in the fifth embodiment. Therefore, only said high oxygen partial pressure condition will be described below.

The "partial pressure of oxygen" in the high oxygen partial pressure condition refers to a value determined as described below. Cardiomyocytes are seeded in a 96-well plate and cultured in a culture medium to produce a cardiomyocyte sheet. A new culture medium is added to the cardiomyocytes sheet, so that the same cardiomyocyte-containing culture medium as that used in the drug response testing is prepared in triplicate using three wells. Each of the cardiomyocyte-containing culture media is left to stand for 0.5 or more hours after being prepared. Thereafter, the partial pressure of oxygen of each of the cardiomyocyte-containing culture media is measured using the extracellular flux analyzer XFe96 (Agilent Technologies), and an average value is determined. The value determined in this manner is referred to as a partial pressure of oxygen. In this specification, the "cardiomyocyte-containing culture medium" refers to a culture medium containing the cardiomyocytes used in the drug response testing (generally in a state where the cardiomyocytes are adhered to the bottom surface of the culture vessel) but not containing the drug used in the drug response testing.

A value of the partial pressure of oxygen of the cardiomyocyte-containing culture medium is not stable immediately after the cardiomyocyte-containing culture medium is prepared. Therefore, the partial pressure of oxygen of the cardiomyocyte-containing culture medium is measured after the cardiomyocyte-containing culture medium is left to stand for 0.5 or more hours after being prepared, as described above. Also, the measured value of the partial pressure of oxygen increases temporarily because the liquid surface of the culture medium is shaken by putting a measuring device in the culture medium when measuring the partial pressure of oxygen. Therefore, a value measured 12 or more minutes after the measuring device is put in the culture medium is adopted as the measured value. That is, the measurement is performed after the shaking of the liquid surface of the culture medium stops completely.

Whether or not the cardiomyocyte-containing culture medium satisfies the high oxygen partial pressure condition, that is, whether or not the cardiomyocyte-containing culture medium is maintained to have a partial pressure of oxygen of 125 mmHg or more in the absence of a drug can be confirmed as described below. Specifically, if the partial pressure of oxygen of the cardiomyocyte-containing culture medium that is determined after the cardiomyocyte-containing culture medium is left to stand for about 0.5 hour after being prepared is 125 mmHg or more, it is determined that the cardiomyocyte-containing culture medium satisfies the high oxygen partial pressure condition. Thus, if it is confirmed that the partial pressure of oxygen shows a predetermined value of 125 mmHg or more at a representative point of time when the value of the partial pressure of oxygen is stable (i.e., about 0.5 hour after preparing the cardiomyocyte-containing culture medium), it can be considered that the partial pressure of oxygen of the culture medium is maintained at a value that is almost the same as the predetermined value at other points in time as well by virtue of the environment in which the culture medium is replenished with oxygen from the atmosphere even when the cardiomyocytes consume the oxygen in the culture medium (see Example 7 below).

The "high oxygen partial pressure condition" is preferably "a condition in which the cardiomyocyte-containing culture medium is maintained to have a partial pressure of oxygen of 130 mmHg or more in the absence of a drug", more preferably "a condition in which the cardiomyocyte-containing culture medium is maintained to have a partial pressure of oxygen of 135 mmHg or more in the absence of a drug", even more preferably "a condition in which the cardiomyocyte-containing culture medium is maintained to have a partial pressure of oxygen of 140 mmHg or more in the absence of a drug", and still more preferably "a condition in which the cardiomyocyte-containing culture medium is maintained to have a partial pressure of oxygen of 145 mmHg or more in the absence of a drug". The upper limit of the partial pressure of oxygen is, for example, 760 mmHg.

Whether or not the cardiomyocyte-containing culture medium satisfies the above-described preferable high oxygen partial pressure conditions, that is, whether or not the cardiomyocyte-containing culture medium is maintained to have a partial pressure of oxygen of X mmHg or more in the absence of a drug can be confirmed as described above. Specifically, if a value of the partial pressure of oxygen of the cardiomyocyte-containing culture medium that is determined after the cardiomyocyte-containing culture medium is left to stand for about 0.5 hour after being prepared is X mmHg or more, it is determined that the cardiomyocyte-containing culture medium satisfies the preferable high oxygen partial pressure conditions.

When the partial pressure of oxygen is represented in units of Pascals, the "high oxygen partial pressure condition" is "a condition in which the cardiomyocyte-containing culture medium is maintained to have a partial pressure of oxygen of 16.7 kPa or more (i.e., 125 mmHg or more) in the absence of a drug", preferably "a condition in which the cardiomyocyte-containing culture medium is maintained to have a partial pressure of oxygen of 17.3 kPa or more (i.e., 130 mmHg or more) in the absence of a drug", more preferably "a condition in which the cardiomyocyte-containing culture medium is maintained to have a partial pressure of oxygen of 18.0 kPa or more (i.e., 135 mmHg or more) in the absence of a drug", even more preferably, "a condition in which the cardiomyocyte-containing culture medium is maintained to have a partial pressure of oxygen of 18.7 kPa or more (i.e., 140 mmHg or more) in the absence of a drug", and still more preferably, "a condition in which the cardiomyocyte-containing culture medium is maintained to have a partial pressure of oxygen of 19.3 kPa or more (i.e., 145 mmHg or more) in the absence of a drug".

The "high oxygen partial pressure condition" can be produced by adopting a configuration affecting the partial pressure of oxygen of the culture medium so as to increase the partial pressure of oxygen. The "configuration affecting the partial pressure of oxygen of the culture medium" can be referred to the first to third embodiments described above and sixth to ninth embodiments described below. Examples of the "configuration affecting the partial pressure of oxygen of the culture medium" include addition of the oxygen carrier to the culture medium, reduction of the distance from the liquid surface of the culture medium to the bottom surface of the culture vessel contacted by the cardiomyocyte (hereinafter also referred to a "liquid-surface distance"), and use of the container having an oxygen permeability.

The "high oxygen partial pressure condition" can be produced by, for example, reducing the liquid-surface distance. Specifically, the "high oxygen partial pressure condition" can be produced by setting the liquid-surface distance to 5.0 mm or less, preferably 3.5 mm or less, more preferably 1.5 mm or less, and even more preferably 1.0 mm or less. The lower limit of the liquid-surface distance is, for example, 0.1 mm.

The "high oxygen partial pressure condition" can be produced preferably by reducing the liquid-surface distance and adjusting the cell density. Specifically, the "high oxygen partial pressure condition" can be produced by setting the liquid-surface distance to 1.5 mm or less when the cell density of the cardiomyocytes is equal to or greater than $2.5 \times 10^5$ cells/cm$^2$. Alternatively, the "high oxygen partial pressure condition" can be produced by setting the liquid-surface distance to 3.5 mm or less when the cell density of the cardiomyocytes is equal to or greater than $1.25 \times 10^5$ cells/cm$^2$, and less than $2.5 \times 10^5$ cells/cm$^2$. Alternatively, the "high oxygen partial pressure condition" can be produced by setting the liquid-surface distance to 5.0 mm or less when the cell density of the cardiomyocytes is equal to or greater than $0.625 \times 10^5$ cells/cm$^2$, and less than $1.25 \times 10^5$ cells/cm$^2$.

In the fifth embodiment, the "high oxygen partial pressure condition" is adopted in the drug response testing; thereby, the effects described below can be achieved. That is, it is possible to suppress the occurrence of an arrest of the pulsation of the cardiomyocyte during the drug response testing (see Example 7 below). It is also possible to detect the change in the waveform caused by the addition of the drug (e.g., prolongation of the duration of the action potential waveform or the $Ca^{2+}$ waveform, which corresponds to QT prolongation, arrhythmia due to EAD, or the like) as a more distinct change in the waveform (see Example 7 below).

It is considered that since the "high oxygen partial pressure condition" is adopted in the fifth embodiment, the rate of oxygen supply to the cardiomyocyte is increased, allowing the cardiomyocyte to properly exhibit the drug-response effect.

1-7. Other Embodiments

Other examples of the "measure to increase a rate of oxygen supply to the cardiomyocyte" will be described below. Hereinafter, only the portions different from the first embodiment will be described, and descriptions of the portions overlapping with the first embodiment will be omitted.

According to a sixth embodiment, there is provided a method for testing drug response of a cardiomyocyte, the method including:

testing a response of the cardiomyocyte to an added drug in a culture medium placed under a high oxygen concentration atmosphere; or testing a response of the cardiomyocyte to an added drug immediately after placing the cardiomyocyte in a culture medium placed under a high oxygen concentration atmosphere.

In the sixth embodiment, the drug response testing is performed in a culture medium placed under a high oxygen concentration atmosphere or performed immediately after placing the cardiomyocyte in a culture medium placed under a high oxygen concentration atmosphere. The high oxygen concentration atmosphere can be produced specifically by covering a culture vessel containing a culture medium with an airtight box to isolate the culture vessel from the atmosphere and filling the inside of the isolated culture vessel with a gas having a high oxygen concentration. For example, a microscope incubator, a microscope chamber, or the like may be used as the airtight box. Also, the high oxygen concentration atmosphere can be maintained by using a device (oxygen controller) that controls an oxygen concentration in a sealed space.

The high oxygen concentration atmosphere refers to an atmosphere having an oxygen concentration higher than the oxygen concentration in the air (i.e., about 20% by volume), and is, for example, an atmosphere having an oxygen concentration of 25 to 100% by volume.

According to a seventh embodiment, there is provided a method for testing drug response of a cardiomyocyte, the method including:

testing a response of the cardiomyocyte to an added drug in a culture medium while bubbling an oxygen-containing gas into the culture medium, or testing a response of the cardiomyocyte to an added drug immediately after placing the cardiomyocyte in a culture medium into which an oxygen-containing gas is being bubbled.

In the seventh embodiment, the drug response testing is performed while bubbling an oxygen-containing gas into a culture medium, or performed immediately after placing the cardiomyocyte in a culture medium into which an oxygen-containing gas is being bubbled. Specifically, the bubbling of an oxygen-containing gas may be performed by inserting a tube into the culture medium and sending an oxygen-containing gas to the culture medium. The rate of bubbling may be, for example, 0.1 to 1000 mL/minute. The oxygen-containing gas may be air, a gas having an oxygen concentration of 25% by volume or more, or oxygen gas.

According to an eighth embodiment, there is provided a method for testing drug response of a cardiomyocyte, the method including:

testing a response of the cardiomyocyte to an added drug in a culture medium while shaking the culture medium, or testing a response of the cardiomyocyte to an added drug immediately after placing the cardiomyocyte in a shaking culture medium.

In the eighth embodiment, the drug response testing is performed while shaking a culture medium or performed immediately after placing the cardiomyocyte in a shaking culture medium. Shaking the culture medium causes the liquid surface of the culture medium to shake and increases the contact between the atmosphere and the culture medium, making it possible to increase the oxygen concentration in the culture medium. Also, as the culture medium is stirred by the shaking, the oxygen which tends to converge in a part of the culture medium near the liquid surface can be dispersed uniformly to reach a part of the culture medium near the cells. Specifically, the shaking can be performed using a shaking culture apparatus for a culture dish or a microtiter plate. The shaking conditions may be, for example, 1 to 1000 cm in amplitude and 1 to 1000 rpm in velocity.

According to a ninth embodiment, there is provided a method for testing drug response of a cardiomyocyte, the method including:

testing a response of the cardiomyocyte to an added drug in a culture medium having a high amount of dissolved oxygen in a circulation-type culture system that supplies the culture medium, or testing a response of the cardiomyocyte to an added drug immediately after placing the cardiomyocyte in a culture medium having a high amount of dissolved oxygen in a circulation-type culture system that supplies the culture medium.

In the ninth embodiment, the drug response testing is performed in a culture medium having a high amount of dissolved oxygen in a circulation-type culture system that supplies the culture medium, or performed immediately after placing the cardiomyocyte in a culture medium having a high amount of dissolved oxygen in a circulation-type culture system that supplies the culture medium. Specifically, this embodiment can be performed by supplying a culture medium having a high amount of dissolved oxygen to the cardiomyocyte using a perfusion culture apparatus. The amount of dissolved oxygen in the culture medium may be, for example, 3 to 1000 mg/L, and the circulation rate of the culture medium may be, for example, 1 to 1000 ml/minute.

It is considered that the rate of oxygen supply to the cardiomyocyte is increased in the above-described sixth to ninth embodiments as well by adopting the measures shown in the respective embodiments, and it is considered that the increase in the rate of oxygen supply to the cardiomyocyte allows the cardiomyocyte to properly exhibit the drug-response effect in the drug response testing.

It is already stated above that the first embodiment and the second embodiment may be combined when implemented; however, the combination is not limited thereto. The first embodiment to the ninth embodiment described above may be suitably combined, if technically possible.

2. Other Aspects 2-1. Method for Testing Response of Cardiomyocyte to Change in Culture Environment The methods of the first to ninth embodiments described above, which are methods for testing a response of a cardiomyocyte to a change in a culture environment caused by the addition of a drug, can be generalized to methods for testing a response of a cardiomyocyte to any change in a culture environment, such as a change in the temperature of the culture medium, a change in the salt concentration of the culture medium, a change in the pH of the culture medium, or the like.

The methods of the first to ninth embodiments adopt the configuration for increasing the amount of oxygen supplied to the cardiomyocyte, thereby increasing the rate of oxygen supply to the cardiomyocyte, and as a result allowing the cardiomyocyte to properly exhibit the drug-response effect. Accordingly, it is considered that adopting the configuration for increasing the amount of oxygen supplied to the cardiomyocyte according to the methods of the first to ninth embodiments increases the rate of oxygen supply to the cardiomyocyte and as a result properly exhibits the response effect of the cardiomyocyte to any change in a culture environment.

Said "any change in a culture environment" includes not only a change in the composition of the culture medium caused by the addition of a drug, but also a change in the temperature of the culture medium, a change in the salt concentration of the culture medium, a change in the pH of the culture medium, and the like. It has been observed that when the temperature of a cardiomyocyte culture medium is lowered or raised from 37° C., which is the temperature of a normal cell-culture environment, to a temperature in a range of 20° C. to 43° C., for example, the number of pulsations of the cardiomyocyte is decreased or increased, and the pulsation stops at a certain low temperature or high temperature. It has also been observed that when the pH of a cardiomyocyte culture medium is lowered or raised from a value in a range of 7.0 to 7.4, which is the pH of a normal cell-culture environment, to a value in a range of 6.0 to 9.0, for example, the number of pulsations of the cardiomyocyte is decreased or increased, and the pulsation stops under certain pH conditions. Furthermore, it has been observed that when the KCl salt concentration of a cardiomyocyte culture medium is decreased or increased from about 5 mM, which is the KCl salt concentration of a normal cell-culture environment, to a KCl salt concentration in a range of 0 mM to 100 mM, for example, the number of pulsations of the cardiomyocyte is decreased or increased, and the pulsation stops under certain KCl salt concentration conditions. Even under such a culture environment, where a decrease or an increase in the number of pulsations and an arrest of the pulsation are observed, the response effect of the cardiomyocyte to a change in a culture environment can be properly exhibited by adopting the configuration for increasing the amount of oxygen supplied to the cardiomyocyte according to the methods of the first to ninth embodiments (see Example 8 below).

Thus, the first embodiment may be generalized to the following method:

a method for testing a response of a cardiomyocyte to a change in a culture environment, the method including:

testing a response of the cardiomyocyte to a change in a culture environment in a culture medium under a condition in which a distance from a liquid surface of the culture medium to a bottom surface of a culture vessel contacted by the cardiomyocyte is 5.0 mm or less; or testing a response of the cardiomyocyte to a change in a culture environment immediately after placing the cardiomyocyte in a culture medium under a condition in which a distance from a liquid surface of the culture medium to a bottom surface of a culture vessel contacted by the cardiomyocyte is 5.0 mm or less.

The second embodiment may be generalized to the following method:

a method for testing a response of a cardiomyocyte to a change in a culture environment, the method including:

testing a response of the cardiomyocyte to a change in a culture environment in a culture medium containing an oxygen carrier; or testing a response of the cardiomyocyte to a change in a culture environment immediately after placing the cardiomyocyte in a culture medium containing an oxygen carrier.

The third embodiment may be generalized to the following method:

a method for testing a response of a cardiomyocyte to a change in a culture environment, the method including:

testing a response of the cardiomyocyte to a change in a culture environment in a culture medium contained in a container having an oxygen permeability; or testing a response of the cardiomyocyte to a change in a culture environment immediately after placing the cardiomyocyte in a culture medium contained in a container having an oxygen permeability.

The fourth embodiment may be generalized to the following method:

a method for testing a response of a cardiomyocyte to a change in a culture environment, the method including:

testing a response of the cardiomyocyte to a change in a culture environment in a culture medium under a measure to increase a rate of oxygen supply to the cardiomyocyte; or testing a response of the cardiomyocyte to a change in a culture environment immediately after placing the cardiomyocyte in a culture medium under a measure to increase a rate of oxygen supply to the cardiomyocyte.

The fifth embodiment may be generalized to the following method:

a method for testing a response of a cardiomyocyte to a change in a culture environment, the method including:

testing a response of the cardiomyocyte to a change in a culture environment under a condition in which a cardiomyocyte-containing culture medium is maintained to have a partial pressure of oxygen of 125 mmHg or more in the absence of a drug; or testing a response of the cardiomyocyte to a change in a culture environment immediately after placing the cardiomyocyte under a condition in which a cardiomyocyte-containing culture medium is maintained to have a partial pressure of oxygen of 125 mmHg or more in the absence of a drug.

The sixth to ninth embodiments may be generalized to the following method:

a method for testing a response of a cardiomyocyte to a change in a culture environment, the method including:

a) testing a response of the cardiomyocyte to a change in a culture environment in a culture medium placed under a high oxygen concentration atmosphere, or testing a response of the cardiomyocyte to a change in a culture environment immediately after placing the cardiomyocyte in a culture medium placed under a high oxygen concentration atmosphere;

b) testing a response of the cardiomyocyte to a change in a culture environment in a culture medium while bubbling an oxygen-containing gas into the culture medium, or testing a response of the cardiomyocyte to a change in a culture environment immediately after placing the cardiomyocyte in a culture medium into which an oxygen-containing gas is being bubbled;

c) testing a response of the cardiomyocyte to a change in a culture environment in a culture medium while shaking the culture medium, or testing a response of the cardiomyocyte to a change in a culture environment immediately after placing the cardiomyocyte in a shaking culture medium; or d) testing a response of the cardiomyocyte to a change in a culture environment in a culture medium having a high amount of dissolved oxygen in a circulation-type culture system that supplies the culture medium, or testing a response of the cardiomyocyte to a change in a culture environment immediately after placing the cardiomyocyte in a culture medium having a high amount of dissolved oxygen in a circulation-type culture system that supplies the culture medium.

The generalized methods described above can be performed according to the same procedures as in the first to ninth embodiments. If the change in the culture environment is a change in the temperature of the culture medium, the temperature of the cardiomyocyte culture medium can be varied within a range of 20 to 43° C., for example. If the change in the culture environment is a change in the pH of the culture medium, the pH of the cardiomyocyte culture medium can be varied within a range of 6.0 to 9.0, for example. If the change in the culture environment is a change in the salt concentration of the culture medium, the KCl salt concentration can be varied within a range of 0 to 100 mM, for example.

2-2. Culture Medium for Drug Response Testing

According to another aspect, there is provided a culture medium for drug response testing that includes a culture medium for cardiomyocytes, and an oxygen carrier. In this aspect, the "culture medium for cardiomyocytes" is the "culture medium for adding an oxygen carrier" described in the first embodiment, and the "oxygen carrier" is as described in the first embodiment. In the culture medium for drug response testing, the oxygen carrier is dissolved in the culture medium for cardiomyocytes.

The culture medium for drug response testing includes:

a culture medium for cardiomyocytes; and an oxygen carrier, preferably an oxygen-carrying protein, more preferably hemoglobin.

The culture medium for drug response testing includes:

a culture medium for cardiomyocytes; and an oxygen carrier in an amount of preferably 0.1 to 10% by mass, more preferably 0.5 to 5.0% by mass, and still more preferably 2.0 to 5.0% by mass with respect to the culture medium for cardiomyocytes, wherein the oxygen carrier is preferably an oxygen-carrying protein, more preferably hemoglobin.

Preferably, the culture medium for drug response testing includes:

a culture medium for cardiomyocytes that is composed of a basal medium such as DMEM, RPMI, IMDM, Ham-12, or the like; and an oxygen carrier, preferably an oxygen-carrying protein, more preferably hemoglobin. Herein, the content of the oxygen carrier in the culture medium for cardiomyocytes is preferably 0.1 to 10% by mass, more preferably 0.5 to 5.0% by mass, and still more preferably 2.0 to 5.0% by mass with respect to the culture medium for cardiomyocytes.

Alternatively, the culture medium for drug response testing preferably includes:

a culture medium for cardiomyocytes that is composed of 0.01 to 0.5 g/L of $CaCl_2$, 0 to 1.0 g/L of $MgSO_4$, 0.1 to 1.0 g/L of KCl, 0 to 10.0 g/L of $NaHCO_3$, 1.0 to 20.0 g/L of NaCl, 0 to 1.0 g/L of $Na_2HPO_4$, and 0 to 20.0 g/L of HEPES; and an oxygen carrier, preferably an oxygen-carrying protein, and more preferably hemoglobin. Herein, the culture medium for cardiomyocytes may contain no serum, or may further contain serum in an amount of 40% by mass or less with respect to the culture medium for cardiomyocytes. Also herein, the content of the oxygen carrier in the culture medium for cardiomyocytes is preferably 0.1 to 10% by mass, more preferably 0.5 to 5.0% by mass, and still more preferably 2.0 to 5.0% by mass with respect to the culture medium for cardiomyocytes.

As an example, the culture medium for drug response testing includes:

a culture medium for cardiomyocytes that is composed of
0.182 g/L of $CaCl_2$,
0.09767 g/L of $MgSO_4$,
0.4 g/L of KCl,
3.362 g/L of $NaHCO_3$,
5.4525 g/L of NaCl,
0.109 g/L of $Na_2HPO_4$, and
5.958 g/L of HEPES; and an oxygen carrier, preferably an oxygen-carrying protein, and more preferably hemoglobin. Herein, the culture medium for cardiomyocytes may contain no serum, or may further contain serum in an amount of 40% by mass or less with respect to the culture medium for cardiomyocytes. Also herein, the content of the oxygen carrier in the culture medium for cardiomyocytes is preferably 0.1 to 10% by mass, more preferably 0.5 to 5.0% by mass, and still more preferably 2.0 to 5.0% by mass with respect to the culture medium for cardiomyocytes.

The pH of the culture medium for drug response testing is not particularly limited; however, it is preferably from 6.0 to 9.0, and more preferably from 7.0 to 8.0.

2-3. Kit for Drug Response Testing

According to still another aspect, there is provided a kit for drug response testing that includes a culture medium for cardiomyocytes, and an oxygen carrier. In this aspect, the "culture medium for cardiomyocytes" is the "culture medium for adding an oxygen carrier" described in the first embodiment, and the "oxygen carrier" is as described in the first embodiment. The kit for drug response testing includes a culture medium for cardiomyocytes, and an oxygen carrier in separate packages. Therefore, the above-described culture medium for drug response testing can be obtained by mixing the "culture medium for cardiomyocytes" and the "oxygen carrier" that are included in the kit for drug response testing and dissolving the oxygen carrier in the culture medium for cardiomyocytes.

The kit for drug response testing includes:
a culture medium for cardiomyocytes; and
an oxygen carrier, preferably an oxygen-carrying protein, and more preferably hemoglobin.

The kit for drug response testing includes:
a culture medium for cardiomyocytes; and
an oxygen carrier in an amount of preferably 0.1 to 10% by mass, and more preferably 0.5 to 5.0% by mass with respect to the culture medium for cardiomyocytes, wherein the oxygen carrier is preferably an oxygen-carrying protein, more preferably hemoglobin.

Preferably, the kit for drug response testing includes:
a culture medium for cardiomyocytes that is composed of a basal medium such as DMEM, RPMI, IMDM, Ham-12, or the like; and
an oxygen carrier, preferably an oxygen-carrying protein, and more preferably hemoglobin. Herein, the content of the oxygen carrier in the culture medium for cardiomyocytes is preferably 0.1 to 10% by mass, and more preferably 0.5 to 5.0% by mass with respect to the culture medium for cardiomyocytes.

Alternatively, the kit for drug response testing preferably includes:
a culture medium for cardiomyocytes that is composed of
0.01 to 0.5 g/L of $CaCl_2$,
0 to 1.0 g/L of $MgSO_4$,
0.1 to 1.0 g/L of KCl,
0 to 10.0 g/L of $NaHCO_3$,
1.0 to 20.0 g/L of NaCl,
0 to 1.0 g/L of $Na_2HPO_4$, and
0 to 20.0 g/L of HEPES; and an oxygen carrier, preferably an oxygen-carrying protein, and more preferably hemoglobin. Herein, the culture medium for cardiomyocytes may contain no serum, or may further contain serum in an amount of 40% by mass or less with respect to the culture medium for cardiomyocytes. Also herein, the content of the oxygen carrier in the culture medium for cardiomyocytes is preferably 0.1 to 10% by mass, and more preferably 0.5 to 5.0% by mass with respect to the culture medium for cardiomyocytes.

As an example, the kit for drug response testing includes:
a culture medium for cardiomyocytes that is composed of
0.182 g/L of $CaCl_2$,
0.09767 g/L of $MgSO_4$,
0.4 g/L of KCl,
3.362 g/L of $NaHCO_3$,
5.4525 g/L of NaCl,
0.109 g/L of $Na_2HPO_4$, and
5.958 g/L of HEPES; and an oxygen carrier, preferably an oxygen-carrying protein, and more preferably hemoglobin. Herein, the culture medium for cardiomyocytes may contain no serum, or may further contain serum in an amount of 40% by mass or less with respect to the culture medium for cardiomyocytes. Also herein, the content of the oxygen carrier in the culture medium for cardiomyocytes is preferably 0.1 to 10% by mass, and more preferably 0.5 to 5.0% by mass with respect to the culture medium for cardiomyocytes.

2-4. Agent for Inhibiting Pulsation Arrest of Cardiomyocyte and Agent for Enhancing Drug Response of Cardiomyocyte According to still another aspect, there is provided an agent for inhibiting a pulsation arrest of a cardiomyocyte that includes an oxygen carrier, or an agent for enhancing drug response of a cardiomyocyte that includes an oxygen carrier. In this aspect, the "oxygen carrier" is as described in the first embodiment. The agent for inhibiting a pulsation arrest of a cardiomyocyte can be used in the drug response testing of a cardiomyocyte by being added to a culture medium for cardiomyocytes. Likewise, the agent for enhancing drug response of a cardiomyocyte can be used in the drug response testing of a cardiomyocyte by being added to a culture medium for cardiomyocytes.

The dosage form of the agent for inhibiting a pulsation arrest of a cardiomyocyte or the agent for enhancing drug response of a cardiomyocyte according to the present invention is not particularly limited. If the agent for inhibiting or the agent for enhancing contains an oxygen-carrying protein, for example, the dosage form thereof may be the same as the general form in which hemoglobin is sold, such as a powder form, a form of an aqueous solution contained in a plastic container, or the like.

The present invention also includes use of the above-described oxygen carrier for inhibiting an arrest of pulsation of a cardiomyocyte, or use of the above-described oxygen carrier for enhancing drug response of a cardiomyocyte.

The present invention is not limited to the above-described embodiments and can be modified in various manners in practice without departing from the gist of the invention. The respective embodiments may be suitably combined, in which case a combined effect will be achieved. Furthermore, the above-described embodiments include various inventions, and various inventions can be derived by combinations of elements selected from the plurality of disclosed elements. For example, even if some of the elements disclosed in an embodiment are deleted, a configuration excluding those elements can be derived as an invention as long as the problem can be solved and the effect can be achieved.

3. Preferred Embodiments

The preferred embodiments of the present invention are summarized below.

As described above, according to the first embodiment, there is provided a method for testing drug response of a cardiomyocyte, the method comprising:

testing a response of the cardiomyocyte to an added drug in a culture medium containing an oxygen carrier; or testing a response of the cardiomyocyte to an added drug immediately after placing the cardiomyocyte in a culture medium containing an oxygen carrier.

According to a preferred embodiment, in the first embodiment, the method comprises:

testing a response of the cardiomyocyte to an added drug in a culture medium containing an oxygen carrier.

As described above, according to the second embodiment, there is provided a method for testing drug response of a cardiomyocyte, the method comprising:

testing a response of the cardiomyocyte to an added drug in a culture medium under a condition in which a distance from a liquid surface of the culture medium to a bottom surface of a culture vessel contacted by the cardiomyocyte is 5.0 mm or less; or testing a response of the cardiomyocyte to an added drug immediately after placing the cardiomyocyte in a culture medium under a condition in which a distance from a liquid surface of the culture medium to a bottom surface of a culture vessel contacted by the cardiomyocyte is 5.0 mm or less.

According to a preferred embodiment, in the second embodiment, the method comprises:

testing a response of the cardiomyocyte to an added drug in a culture medium under a condition in which a distance from a liquid surface of the culture medium to a bottom surface of a culture vessel contacted by the cardiomyocyte is 5.0 mm or less.

As described above, according to the combination of the first embodiment and the second embodiment, there is provided a method for testing drug response of a cardiomyocyte, the method comprising:

testing a response of the cardiomyocyte to an added drug in a culture medium containing an oxygen carrier under a condition in which a distance from a liquid surface of the culture medium to a bottom surface of a culture vessel contacted by the cardiomyocyte is 5.0 mm or less; or testing a response of the cardiomyocyte to an added drug immediately after placing the cardiomyocyte in a culture medium containing an oxygen carrier under a condition in which a distance from a liquid surface of the culture medium to a bottom surface of a culture vessel contacted by the cardiomyocyte is 5.0 mm or less.

According to a preferred embodiment, in the combination of the first embodiment and the second embodiment, the method comprises:

testing a response of the cardiomyocyte to an added drug in a culture medium containing an oxygen carrier under a condition in which a distance from a liquid surface of the culture medium to a bottom surface of a culture vessel contacted by the cardiomyocyte is 5.0 mm or less.

As described above, according to the third embodiment, there is provided a method for testing drug response of a cardiomyocyte, the method comprising:

testing a response of the cardiomyocyte to an added drug in a culture medium contained in a container having an oxygen permeability; or testing a response of the cardiomyocyte to an added drug immediately after placing the cardiomyocyte in a culture medium contained in a container having an oxygen permeability.

According to a preferred embodiment, in the third embodiment, the method comprises:

testing a response of the cardiomyocyte to an added drug in a culture medium contained in a container having an oxygen permeability.

As described above, according to the fourth embodiment, there is provided a method for testing drug response of a cardiomyocyte, the method comprising:

testing a response of the cardiomyocyte to an added drug in a culture medium under a measure to increase a rate of oxygen supply to the cardiomyocyte; or testing a response of the cardiomyocyte to an added drug immediately after placing the cardiomyocyte in a culture medium under a measure to increase a rate of oxygen supply to the cardiomyocyte.

According to a preferred embodiment, in the fourth embodiment, the method comprises:

testing a response of the cardiomyocyte to an added drug in a culture medium under a measure to increase a rate of oxygen supply to the cardiomyocyte.

As described above, according to the fifth embodiment, there is provided a method for testing drug response of a cardiomyocyte, the method comprising:

testing a response of the cardiomyocyte to an added drug under a condition in which a cardiomyocyte-containing culture medium is maintained to have a partial pressure of oxygen of 125 mmHg or more in the absence of a drug; or testing a response of the cardiomyocyte to an added drug immediately after placing the cardiomyocyte under a condition in which a cardiomyocyte-containing culture medium is maintained to have a partial pressure of oxygen of 125 mmHg or more in the absence of a drug.

According to a preferred embodiment, in the fifth embodiment, the method comprises:

testing a response of the cardiomyocyte to an added drug under a condition in which a cardiomyocyte-containing culture medium is maintained to have a partial pressure of oxygen of 125 mmHg or more in the absence of a drug.

As described above, according to the sixth embodiment, there is provided a method for testing drug response of a cardiomyocyte, the method comprising:

testing a response of the cardiomyocyte to an added drug in a culture medium placed under a high oxygen concentration atmosphere; or testing a response of the cardiomyocyte to an added drug immediately after placing the cardiomyocyte in a culture medium placed under a high oxygen concentration atmosphere.

According to a preferred embodiment, in the sixth embodiment, the method comprises:

testing a response of the cardiomyocyte to an added drug in a culture medium placed under a high oxygen concentration atmosphere.

As described above, according to the seventh embodiment, there is provided a method for testing drug response of a cardiomyocyte, the method comprising:

testing a response of the cardiomyocyte to an added drug in a culture medium while bubbling an oxygen-containing gas into the culture medium; or testing a response of the cardiomyocyte to an added drug immediately after placing the cardiomyocyte in a culture medium into which an oxygen-containing gas is being bubbled.

According to a preferred embodiment, in the seventh embodiment, the method comprises:

testing a response of the cardiomyocyte to an added drug in a culture medium while bubbling an oxygen-containing gas into the culture medium.

As described above, according to the eighth embodiment, there is provided a method for testing drug response of a cardiomyocyte, the method comprising:

testing a response of the cardiomyocyte to an added drug in a culture medium while shaking the culture medium; or testing a response of the cardiomyocyte to an added drug immediately after placing the cardiomyocyte in a shaking culture medium.

According to a preferred embodiment, in the eighth embodiment, the method comprises:

testing a response of the cardiomyocyte to an added drug in a culture medium while shaking the culture medium.

As described above, according to the ninth embodiment, there is provided a method for testing drug response of a cardiomyocyte, the method comprising:

testing a response of the cardiomyocyte to an added drug in a culture medium having a high amount of dissolved oxygen in a circulation-type culture system that supplies the culture medium; or testing a response of the cardiomyocyte to an added drug immediately after placing the cardiomyocyte in a culture medium having a high amount of dissolved oxygen in a circulation-type culture system that supplies the culture medium.

According to a preferred embodiment, in the ninth embodiment, the method comprises:

testing a response of the cardiomyocyte to an added drug in a culture medium having a high amount of dissolved oxygen in a circulation-type culture system that supplies the culture medium.

According to a preferred embodiment, in any one of the above-described embodiments, the immediately after is within two hours, preferably within one hour, and more preferably within 30 minutes.

According to a preferred embodiment, in any one of the above-described embodiments, the cardiomyocyte is a cardiomyocyte prepared by inducing differentiation of a pluripotent stem cell, preferably a cardiomyocyte prepared by inducing differentiation of an iPS cell.

According to a preferred embodiment, in any one of the above-described embodiments, the cardiomyocyte is a mammalian cardiomyocyte, preferably a human cardiomyocyte.

According to a preferred embodiment, in any one of the above-described embodiments, the cardiomyocyte is a cardiomyocyte prepared by inducing differentiation of a human iPS cell, preferably a mature cardiomyocyte prepared by inducing differentiation of a human iPS cell.

According to a preferred embodiment, in any one of the above-described embodiments, the cardiomyocyte is in the form of a cardiomyocyte sheet or a cardiomyocyte mass, preferably in the form of a cardiomyocyte sheet.

According to a preferred embodiment, in any one of the above-described embodiments, the oxygen carrier is a red blood cell, an oxygen-carrying protein, or an artificial oxygen carrier, preferably an oxygen-carrying protein, more preferably hemoglobin.

According to a preferred embodiment, in any one of the above-described embodiments, the oxygen carrier is contained in the culture medium in an amount of 0.1 to 10% by mass, preferably 0.5 to 5.0% by mass, more preferably 2.0 to 5.0% by mass, with respect to the culture medium.

According to a preferred embodiment, in any one of the above-described embodiments, the culture medium is a culture medium for cardiomyocytes, such as a culture medium for culturing cardiomyocytes or a culture medium for measuring potential of cardiomyocytes.

According to a preferred embodiment, in any one of the above-described embodiments, the culture medium is contained in a culture vessel, where the culture vessel is a flat-bottomed container.

According to a preferred embodiment, in any one of the above-described embodiments, the drug is a substance known to have effects on cardiomyocytes, or a substance whose effects on cardiomyocytes are desired to be examined.

According to a preferred embodiment, in any one of the above-described embodiments, the drug is a candidate substance for a new drug.

According to a preferred embodiment, in any one of the above-described embodiments, the drug is a candidate substance for a new drug, the cardiomyocyte is a normal cardiomyocyte, and the method further comprises evaluating cardiotoxicity of the candidate substance for a new drug based on the result of the testing.

According to a preferred embodiment, in any one of the above-described embodiments, the drug is a candidate substance for a new drug, the cardiomyocyte is a disease model cardiomyocyte, and the method further comprises evaluating effectiveness of the candidate substance for a new drug for the treatment of the disease based on the result of the testing.

According to a preferred embodiment, in any one of the above-described embodiments, a distance from a liquid surface of the culture medium to a bottom surface of a culture vessel contacted by the cardiomyocyte is 3.5 mm or less, preferably 1.5 mm or less, more preferably 1.0 mm or less.

According to a preferred embodiment, in any one of the above-embodiments, a distance from a liquid surface of the culture medium to a bottom surface of a culture vessel contacted by the cardiomyocyte is 0.1 to 5.0 mm, preferably 0.1 to 3.5 mm, more preferably 0.1 to 1.5 mm or less, still more preferably 0.1 to 1.0 mm.

According to a preferred embodiment, in any one of the above-embodiments, the testing is performed under a condition in which a cardiomyocyte-containing culture medium is maintained to have a partial pressure of oxygen of 125 mmHg or more, preferably 130 mmHg or more, more preferably 135 mmHg or more, still more preferably 140 mmHg or more, still more preferably 145 mmHg or more, in the absence of a drug.

According to a preferred embodiment, in any one of the above-embodiments, the testing is performed under a condition in which a cardiomyocyte-containing culture medium is maintained to have a partial pressure of oxygen of 125 to 760 mmHg, preferably 130 to 760 mmHg, more preferably 135 to 760 mmHg, still more preferably 140 to 760 mmHg, still more preferably 145 to 760 mmHg, in the absence of a drug.

According to a preferred embodiment, in any one of the above-embodiments, a distance from a liquid surface of the culture medium to a bottom surface of a culture vessel contacted by the cardiomyocyte (a liquid-surface distance) is 1.5 mm or less when a cell density of the cardiomyocytes is equal to or greater than $2.5 \times 10^5$ cells/cm$^2$, a distance from a liquid surface of the culture medium to a bottom surface of a culture vessel contacted by the cardiomyocyte (a liquid-surface distance) is 3.5 mm or less when a cell density of the cardiomyocytes is equal to or greater than $1.25 \times 10^5$ cells/cm$^2$, and less than $2.5 \times 10^5$ cells/cm$^2$, and a distance from a liquid surface of the culture medium to a bottom surface of a culture vessel contacted by the cardiomyocyte (a liquid-surface distance) is 5.0 mm or less when a cell density of the cardiomyocytes is equal to or greater than $0.625 \times 10^5$ cells/cm$^2$, and less than $1.25 \times 10^5$ cells/cm$^2$.

As described above, according to another embodiment, there is provided an agent for inhibiting a pulsation arrest of a cardiomyocyte, comprising an oxygen carrier. Also, according to another embodiment, there is provided an agent for enhancing drug response of a cardiomyocyte, comprising an oxygen carrier.

As described above, according to another embodiment, there is provided a kit for drug response testing, comprising a culture medium for cardiomyocytes, and an oxygen carrier. According to a preferred embodiment, in the kit according to the above-described embodiment, the kit comprises the culture medium for cardiomyocytes, and the oxygen carrier in separate packages.

As described above, according to another embodiment, there is provided a culture medium for drug response testing, comprising a culture medium for cardiomyocytes, and an oxygen carrier. According to a preferred embodiment, in the culture medium according to the above-described embodiment, the oxygen carrier is dissolved in the culture medium for cardiomyocytes.

As described above, according to another embodiment, there is provided use of an oxygen carrier for inhibiting an arrest of pulsation of a cardiomyocyte. Also, according to another embodiment, there is provided use of an oxygen carrier for enhancing drug response of a cardiomyocyte.

According to a preferred embodiment, in any one of the above-described embodiments, the oxygen carrier is a red blood cell, an oxygen-carrying protein, or an artificial oxygen carrier, preferably an oxygen-carrying protein, more preferably hemoglobin.

According to a preferred embodiment, in any one of the above-described embodiments, the oxygen carrier is contained in the culture medium in an amount of 0.1 to 10% by mass, preferably 0.5 to 5.0% by mass, more preferably 2.0 to 5.0% by mass, with respect to the culture medium.

According to a preferred embodiment, in any one of the above-described embodiments, the culture medium is a culture medium for cardiomyocytes, such as a culture medium for culturing cardiomyocytes or a culture medium for measuring potential of cardiomyocytes.

EXAMPLES

Example 1 (Conventional Example)

[1-1] Production of Cardiomyocyte Sheets Derived from iPS Cells

Cardiomyocytes were prepared by inducing differentiation of a human iPS cell line (253G1, RIKEN BioResource Center) or a GCaMP gene-transfected human iPS cell line (253G1), which binds to calcium to emit fluorescence, into cardiomyocytes by the method for inducing protein-free cardiac differentiation (PFCD) (see WO2015/182765). The resulting cardiomyocytes were maintained in a myocardial differentiation medium (containing 245 ml of IMDM, 245 ml of DMDM, 5 ml of MEM non-essential amino acid solution (×100), 5 ml of 0.2M L-glutamine, 100 μl of 1M L-carnitine, 50 mg of ascorbic acid, and 1 ml of 0.5M creatine).

The cardiomyocytes were seeded in a 96-well plate about one week prior to conducting drug response testing. Specifically, a trypsin solution (0.25% Trypsin-EDTA (Thermo Fisher Scientific)) was added to treat the cardiomyocytes in an incubator for 5 to 8 minutes. Then, the cardiomyocytes were separated into single cells. The 96-well plate was coated with laminin iMatrix in a concentration of 10 μg/mL, and the single cells were seeded at a cell number of 4 to $8 \times 10^4$ per well. Thereafter, the cardiomyocytes were cultured in a culture medium for 7 days to produce beating cardiomyocyte sheets. The resulting cardiomyocyte sheets were used in the drug response testing. Since the cardiomyocytes do not proliferate during a culture performed to produce a cardiomyocyte sheet, a cell density at the time of seeding is basically maintained in a cardiomyocyte sheet as well when no apparent cell death is seen.

[1-2] Method for Drug Response Testing

Drug response testing was performed by calcium imaging using a fluorescence microscope. Specifically, drug response testing was performed by obtaining a pulsatile calcium fluorescence motion picture of the cardiomyocytes using fluorescence microscope Olympus IX83.

In the drug response testing, a culture medium having the following composition was adjusted to pH 7.4 and used as a culture medium for cardiomyocytes:

0.182 g/L of $CaCl_2$,
0.09767 g/L of $MgSO_4$,
0.4 g/L of KCl,
3.362 g/L of $NaHCO_3$,
5.4525 g/L of NaCl,
0.109 g/L of $Na_2HPO_4$,
5.958 g/L of HEPES; and
10% by mass of FBS (fetal bovine serum, Invitrogen).

In this example, a distance from the liquid surface of the culture medium to the bottom surface of a culture vessel contacted by the cardiomyocytes was 8.33 mm during the drug response testing.

A drug was added to the cell culture medium on a microscope, and calcium signals were measured after 10 minutes by using calcium sensor protein GCaMP or calcium indicator Cal-520. In this specification, a waveform of a measured intracellular calcium ion ($Ca^{2+}$) concentration is referred to as a "$Ca^{2+}$ waveform". ImageJ-based image analysis software was used for data analysis.

Isoproterenol, milrinone, verapamil, E-4031, or terfenadine was used as the drug. Throughout the entire example, the concentration of the drug indicates the final concentration in the culture medium.

[1-3] Results

When isoproterenol was added, an expected drug response (tachycardic response) was detected at a concentration less than a certain concentration (100 nM or more, and less than 200 nM). However, the pulsation occasionally stopped at a concentration equal to or greater than a certain concentration (200 to 1000 nM); thus, it was occasionally impossible to evaluate the drug response waveform.

When milrinone was added, an expected drug response (tachycardic response) was detected at a concentration less than a certain concentration (100 nM or more, and less than 300 nM). However, the pulsation stopped at a concentration equal to or greater than a certain concentration (300 to 500 μM); thus, it was impossible to evaluate the drug response waveform, or an expected drug response (tachycardic response) was not detected.

When verapamil was added, an expected drug response (a decrease in the amplitude of the $Ca^{2+}$ waveform and bradycardic response) was detected at a concentration less than a certain concentration (100 nM or more, and less than 200 nM). However, the pulsation stopped at a concentration equal to or greater than a certain concentration (200 to 500 nM); thus, it was impossible to evaluate the drug response waveform.

When E-4031 was added, an expected drug response (prolongation of the duration of the $Ca^{2+}$ waveform) was detected at a concentration less than a certain concentration (100 nM or more, and less than 300 nM). However, the pulsation stopped at a concentration equal to or greater than a certain concentration (300 to 1000 nM).

When terfenadine was added, an expected drug response (prolongation of the duration of the $Ca^{2+}$ waveform) was detected at a concentration less than a certain concentration (100 nM or more, and less than 300 nM). However, at a concentration equal to or greater than a certain concentration (300 to 1000 nM), the pulsation stopped, or no EAD response, which was expected as a side effect of terfenadine, was observed.

As demonstrated above, the expected drug response could not be evaluated in the drug response testing of cardiomyocytes when the concentration of the added drug exceeded a certain concentration.

Example 2

In Example 2, drug response testing was performed using a culture medium containing hemoglobin.

[2-1] Preparation of Culture Medium

The culture medium containing hemoglobin was prepared by adding 0.5% by mass or 1.0% by mass of bovine hemoglobin (Nacalai tesque 17553-92) to a culture medium having the following composition to suspend the hemoglobin in the culture medium and adjusting the resulting culture medium to pH 7.4 with 5N NaOH or 1N HCl:

0.182 g/L of $CaCl_2$,
0.09767 g/L of $MgSO_4$,
0.4 g/L of KCl,
3.362 g/L of $NaHCO_3$,
5.4525 g/L of NaCl,
0.109 g/L of $Na_2HPO_4$,
5.958 g/L of HEPES; and
10% by mass of FBS (fetal bovine serum, Invitrogen).

A culture medium not containing hemoglobin was prepared in the same manner as the culture medium containing hemoglobin except that hemoglobin was not added.

[2-2] Drug Response Testing

Drug response testing was performed on the samples shown below according to the same procedure as in Example 1. In the same manner as in Example 1, cardiomyocytes were seeded at a cell number of $4\times10^4$ to $8\times10^4$ per well of a 96-well plate (i.e., $1.25\times10^5$ cells/$cm^2$ to $2.5\times10^5$ cells/$cm^2$) and cultured to produce beating cardiomyocyte sheets. The resulting cardiomyocyte sheets were used in the drug response testing.

TABLE 1

|  | Culture medium | Drug |
| --- | --- | --- |
| Sample 2A | Culture medium not containing hemoglobin | 100 nM Isoproterenol |
| Sample 2B | Culture medium not containing hemoglobin | 1000 nM Isoproterenol |
| Sample 2C | Culture medium containing 0.5 mass % of hemoglobin | 100 nM Isoproterenol |
| Sample 2D | Culture medium containing 0.5 mass % of hemoglobin | 1000 nM Isoproterenol |
| Sample 2E | Culture medium containing 1.0 mass % of hemoglobin | 100 nM Isoproterenol |
| Sample 2F | Culture medium containing 1.0 mass % of hemoglobin | 1000 nM Isoproterenol |

In this example, a distance from the liquid surface of the culture medium to the bottom surface of a culture vessel contacted by the cardiomyocytes was 6.67 mm during the drug response testing.

The rate of pulsation arrest was determined as follows:

Pulsation arrest rate (%)={(Number of cardiomyocyte sheets that stopped pulsation within 10 minutes after drug was added)/(Number of cardiomyocyte sheets subjected to drug response testing)}×100

[2-3] Results

When a cardiomyocyte sheet was placed in a culture medium not containing hemoglobin and 100 nM isoproterenol was added, an expected drug response (tachycardic response) was detected and the pulsation did not stop (sample 2A). On the other hand, when a cardiomyocyte sheet was placed in a culture medium not containing hemoglobin and 1000 nM isoproterenol was added, the pulsation stopped at a high frequency (sample 2B).

Figure 2A:
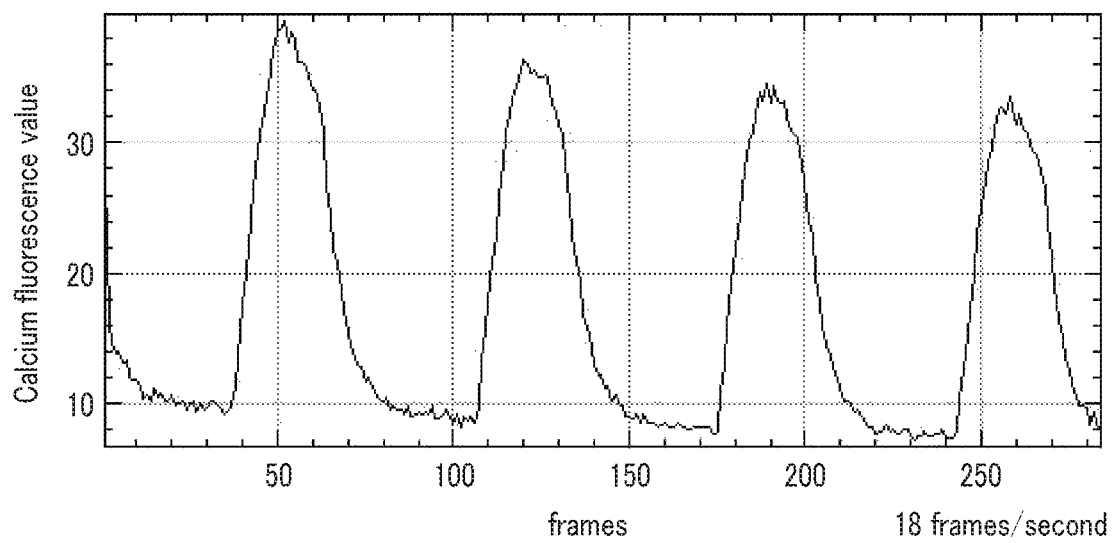
FIG. 2A is a waveform diagram of a sample 2D before addition of a drug.
Figure 2B:
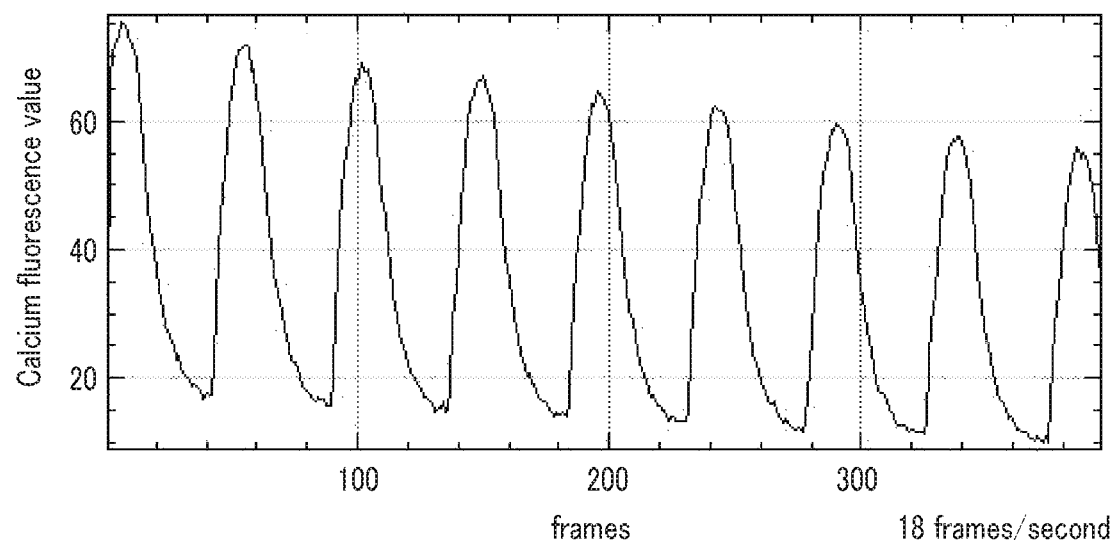
FIG. 2B is a waveform diagram of the sample 2D after addition of the drug.

When a cardiomyocyte sheet was placed in a culture medium containing hemoglobin at a concentration of 0.5% by mass and 100 nM isoproterenol was added, an expected drug response was detected and the pulsation did not stop (sample 2C). Also, even when a cardiomyocyte sheet was placed in a culture medium containing hemoglobin at a concentration of 0.5% by mass and 1000 nM isoproterenol was added, an expected drug response was detected and the pulsation did not stop at all (sample 2D). The results of sample 2D are shown in FIGS. 2A and 2B. FIG. 2A shows the waveform before the addition of the drug, and FIG. 2B shows the waveform after the addition of the drug.

When a cardiomyocyte sheet was placed in a culture medium containing hemoglobin at a concentration of 1.0% by mass and 100 nM isoproterenol was added, an expected drug response was detected and the pulsation did not stop (sample 2E). Also, even when a cardiomyocyte sheet was placed in a culture medium containing hemoglobin at a concentration of 1.0% by mass and 1000 nM isoproterenol was added, an expected drug response was detected and the pulsation did not stop at all (sample 2F).

Figure 3:
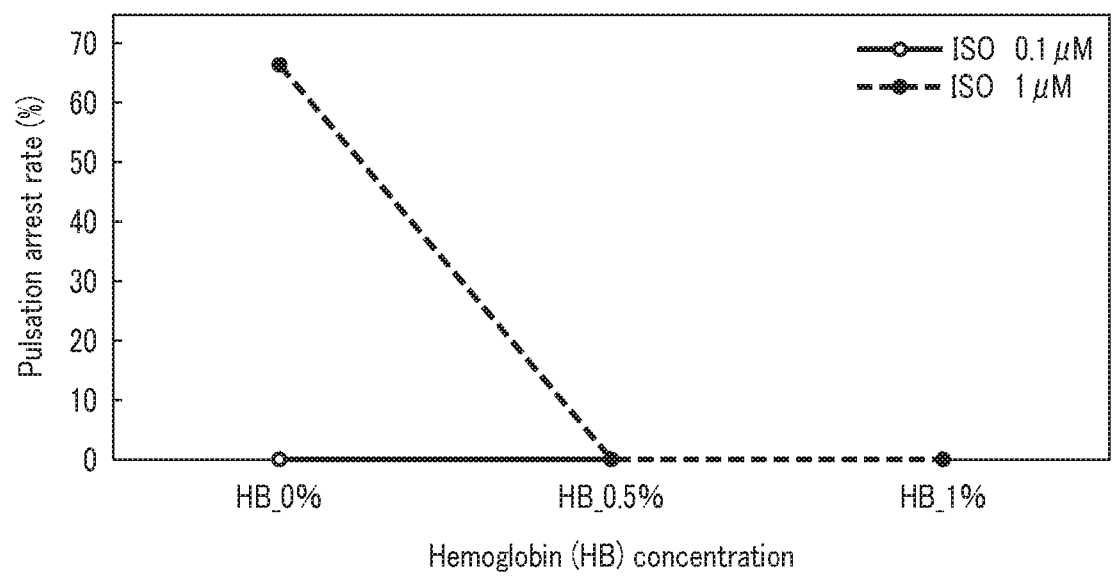
FIG. 3 is a graph showing a relationship between a hemoglobin concentration and a pulsation arrest rate.

The results of samples 2A to 2F are shown together in FIG. 3. FIG. 3 shows the hemoglobin concentration on the horizontal axis and the pulsation arrest rate on the vertical axis. FIG. 3 shows that the occurrence of the pulsation arrest of the cardiomyocytes during the drug response testing can be suppressed by adding hemoglobin to the culture medium. FIG. 3 also shows that the range of the drug concentration applicable in the drug response testing can be extended by adding hemoglobin to the culture medium.

Example 3

In Example 3, drug response testing was performed by varying the distance from the liquid surface of the culture medium (i.e., the liquid surface of the culture medium that is in contact with the atmosphere having an oxygen concentration of about 20% by volume) to the bottom surface of a culture vessel contacted by the cardiomyocytes (see FIG. 1). Said distance was varied by changing the amount of the culture medium. Hereinafter, said distance is also referred to as a "liquid-surface distance".

[3-1] Drug Response Testing

Drug response testing was performed on the samples shown below according to the same procedure as in Example 1. In the same manner as in Example 1, cardiomyocytes were seeded at a cell number of $4 \times 10^4$ to $8 \times 10^4$ per well of a 96-well plate (i.e., $1.25 \times 10^5$ cells/cm$^2$ to $2.5 \times 10^5$ cells/cm$^2$) and cultured to produce beating cardiomyocyte sheets. The resulting cardiomyocyte sheets were used in the drug response testing.

TABLE 2

| | Liquid-surface distance | Drug |
|---|---|---|
| Sample 3A | 8.33 mm | 100 nM Isoproterenol |
| Sample 3B | 8.33 mm | 1000 nM Isoproterenol |
| Sample 3C | 6.67 mm | 100 nM Isoproterenol |
| Sample 3D | 6.67 mm | 1000 nM Isoproterenol |
| Sample 3E | 5.00 mm | 100 nM Isoproterenol |
| Sample 3F | 5.00 mm | 1000 nM Isoproterenol |
| Sample 3G | 3.33 mm | 100 nM Isoproterenol |
| Sample 3H | 3.33 mm | 1000 nM Isoproterenol |
| Sample 3I | 1.67 mm | 100 nM Isoproterenol |
| Sample 3J | 1.67 mm | 1000 nM Isoproterenol |

[3-2] Results

When a cardiomyocyte sheet was placed in a culture medium having a liquid-surface distance of 8.33 mm and 100 nM isoproterenol was added, an expected drug response (tachycardic response) was detected and the pulsation did not stop (sample 3A). On the other hand, when a cardiomyocyte sheet was placed in a culture medium having a liquid-surface distance of 8.33 mm and 1000 nM isoproterenol was added, the pulsation stopped at a high frequency (sample 3B).

Figure 4A:
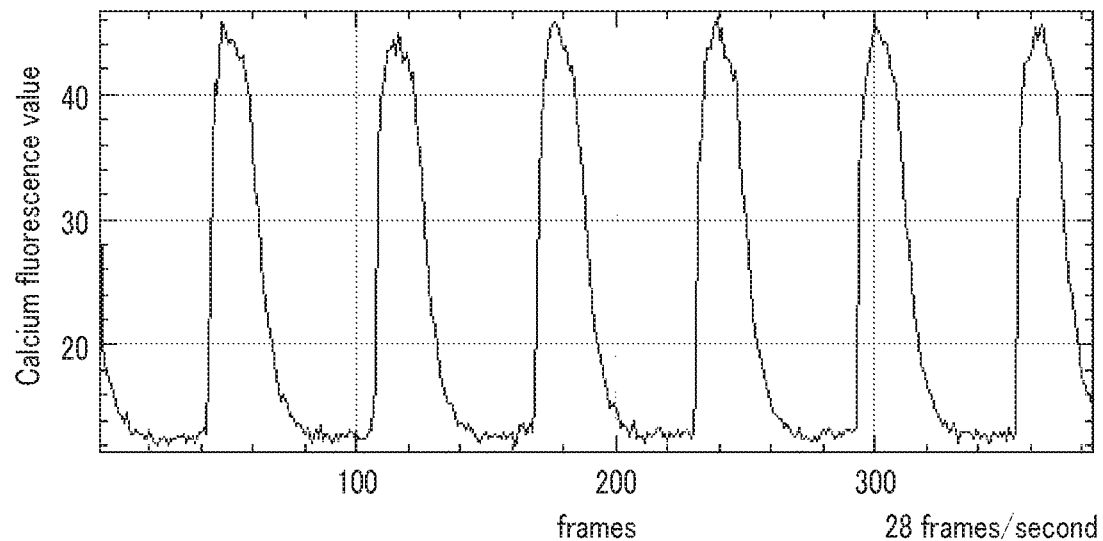
FIG. 4A is a waveform diagram of a sample 3D before addition of a drug.
Figure 4B:
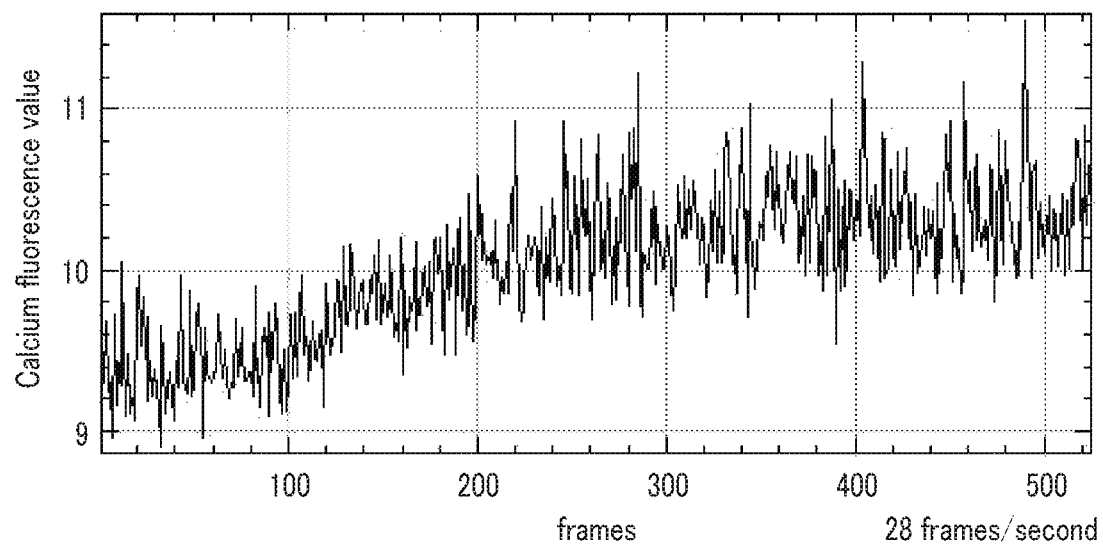
FIG. 4B is a waveform diagram of the sample 3D after addition of the drug.

When a cardiomyocyte sheet was placed in a culture medium having a liquid-surface distance of 6.67 mm and 100 nM isoproterenol was added, an expected drug response was detected and the pulsation did not stop (sample 3C). On the other hand, when a cardiomyocyte sheet was placed in a culture medium having a liquid-surface distance of 6.67 mm and 1000 nM isoproterenol was added, the pulsation stopped at a high frequency (sample 3D). The results of sample 3D are shown in FIGS. 4A and 4B. FIG. 4A shows the waveform before the addition of the drug, and FIG. 4B shows the waveform after the addition of the drug.

When a cardiomyocyte sheet was placed in a culture medium having a liquid-surface distance of 5.00 mm and 100 nM isoproterenol was added, an expected drug response was detected and the pulsation did not stop (sample 3E). On the other hand, when a cardiomyocyte sheet was placed in a culture medium having a liquid-surface distance of 5.00 mm and 1000 nM isoproterenol was added, the frequency of the occurrence of the pulsation arrest was suppressed to about 50% and significantly improved, as compared to the case where the liquid-surface distance was 6.67 mm (sample 3F).

When a cardiomyocyte sheet was placed in a culture medium having a liquid-surface distance of 3.33 mm and 100 nM isoproterenol was added, an expected drug response was detected and the pulsation did not stop (sample 3G). Also, even when a cardiomyocyte sheet was placed in a culture medium having a liquid-surface distance of 3.33 mm and 1000 nM isoproterenol was added, an expected drug response was detected and the pulsation hardly stopped (sample 3H).

Figure 4C:
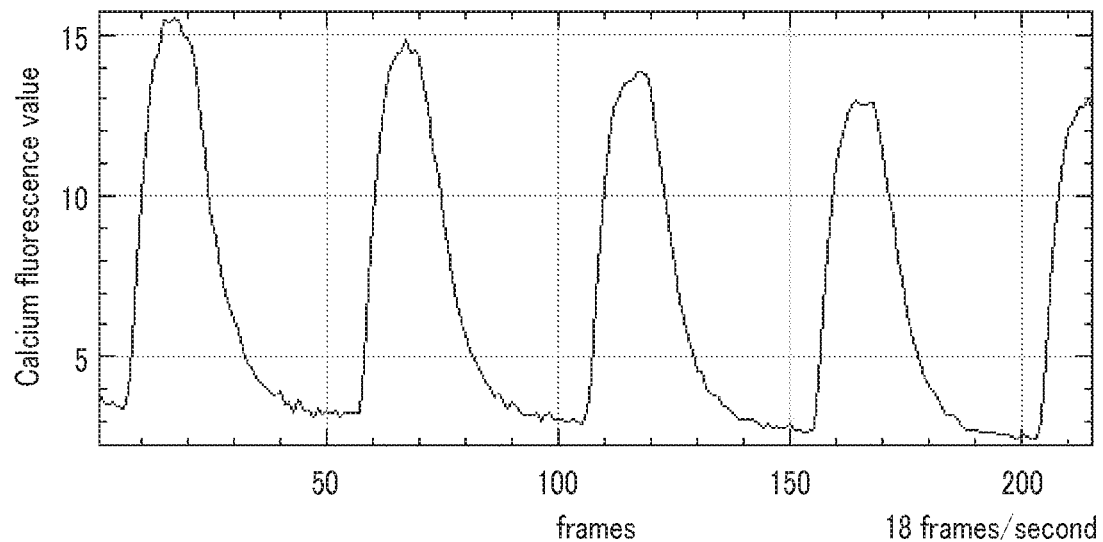
FIG. 4C is a waveform diagram of a sample 3J before addition of a drug.
Figure 4D:
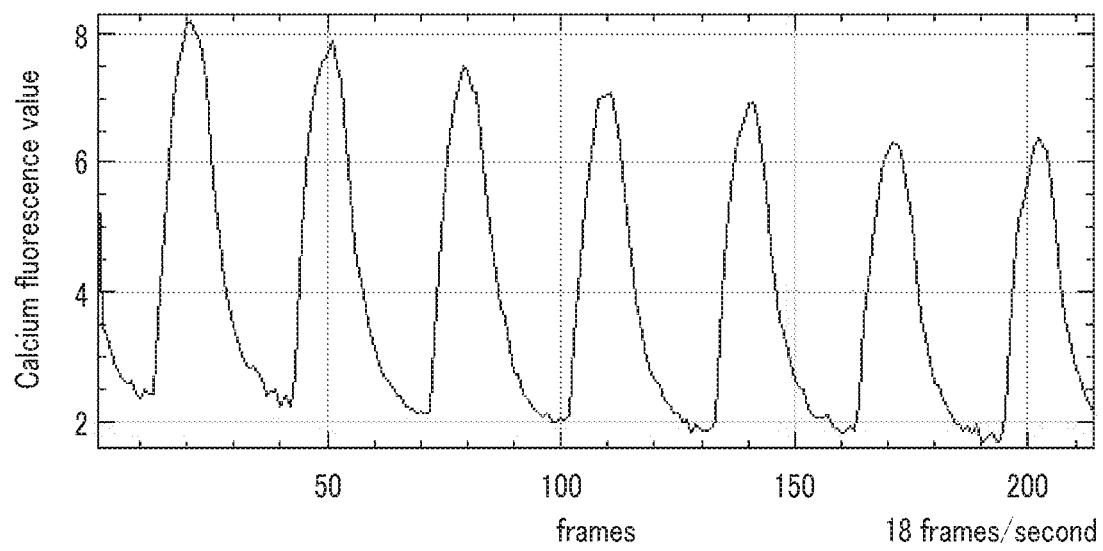
FIG. 4D is a waveform diagram of the sample 3J after addition of the drug.

When a cardiomyocyte sheet was placed in a culture medium having a liquid-surface distance of 1.67 mm and 100 nM isoproterenol was added, an expected drug response was detected and the pulsation did not stop (sample 3I). Also, even when a cardiomyocyte sheet was placed in a culture medium having a liquid-surface distance of 1.67 mm and 1000 nM isoproterenol was added, an expected drug response was detected and the pulsation did not stop at all (sample 3J). The results of sample 3J are shown in FIGS. 4C and 4D. FIG. 4C shows the waveform before the addition of the drug, and FIG. 4D shows the waveform after the addition of the drug.

Figure 5:
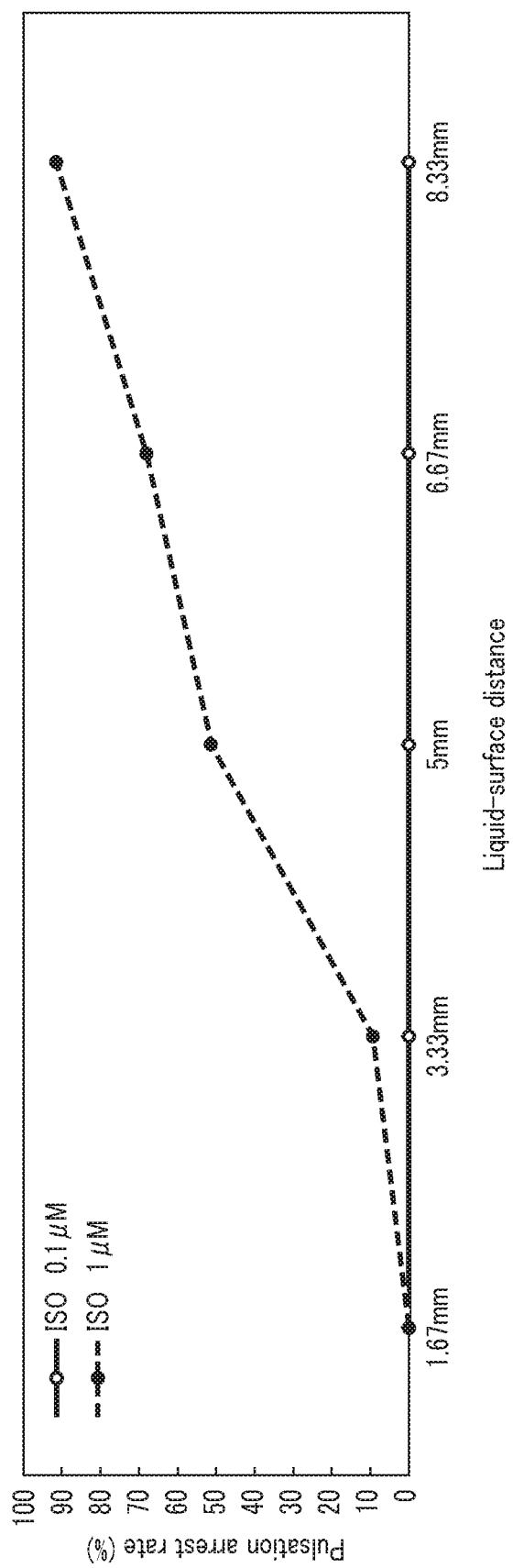
FIG. 5 is a graph showing a relationship between a liquid-surface distance and a pulsation arrest rate.

The results of samples 3A to 3J are shown together in FIG. 5. FIG. 5 shows the liquid-surface distance on the horizontal axis and the pulsation arrest rate on the vertical axis. FIG. 5 shows that the occurrence of the pulsation arrest of the cardiomyocytes during the drug response testing can be suppressed by setting the liquid-surface distance to about 5.0 mm or less, preferably by setting the liquid-surface distance to about 3.5 mm or less. FIG. 5 also shows that the range of the drug concentration applicable in the drug response testing can be extended by setting the liquid-surface distance to about 5.0 mm or less, preferably by setting the liquid-surface distance to about 3.5 mm or less.

Example 4

In Example 4, drug response testing was performed using a culture vessel with a bottom surface having an oxygen permeability (hereinafter also referred to as an "oxygen-permeable container"). Specifically, the VECELL 96-well plate (Vessel Inc.) was used as the oxygen-permeable container. Said container has a gas-permeable film on the bottom surface. The CELLBIND 96-well plate (Corning Incorporated) was used as a control container. Said container is made of a polystyrene material.

[4-1] Drug Response Testing

Drug response testing was performed on the samples shown below according to the same procedure as in Example 1. In the same manner as in Example 1, cardiomyocytes were seeded at a cell number of $4 \times 10^4$ to $8 \times 10^4$ per well of a 96-well plate (i.e., $1.25 \times 10^5$ cells/cm$^2$ to $2.5 \times 10^5$ cells/cm$^2$) and cultured to produce beating cardiomyocyte sheets. The resulting cardiomyocyte sheets were used in the drug response testing.

TABLE 3

| | Culture vessel | Drug |
|---|---|---|
| Sample 4A | Control container | 100 nM Isoproterenol |
| Sample 4B | Control container | 1000 nM Isoproterenol |
| Sample 4C | Oxygen-permeable container | 100 nM Isoproterenol |
| Sample 4D | Oxygen-permeable container | 1000 nM Isoproterenol |

In this example, a distance from the liquid surface of the culture medium to the bottom surface of the culture vessel contacted by the cardiomyocytes was 6.67 mm during the drug response testing.

[4-2] Results

Figure 6A:
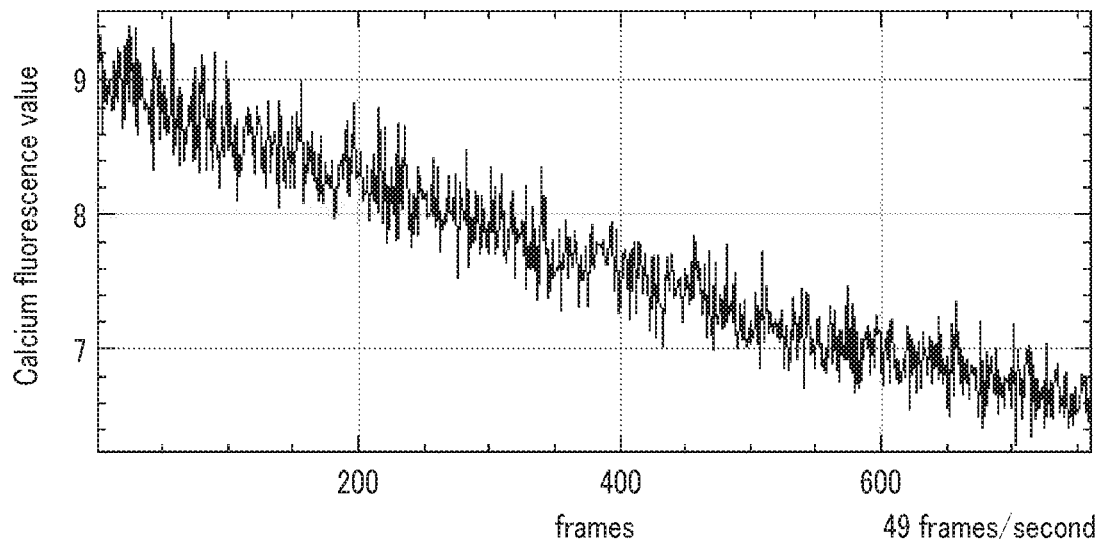
FIG. 6A is a waveform diagram of a sample 4B after addition of a drug.

When a cardiomyocyte sheet was placed in a culture medium contained in the control container and 100 nM isoproterenol was added, an expected drug response (tachycardic response) was detected and the pulsation did not stop (sample 4A). On the other hand, when a cardiomyocyte sheet was placed in a culture medium contained in the control container and 1000 nM isoproterenol was added, the pulsation stopped at a high frequency (sample 4B). The results of sample 4B are shown in FIG. 6A. FIG. 6A shows the waveform after the addition of the drug.

Figure 6B:
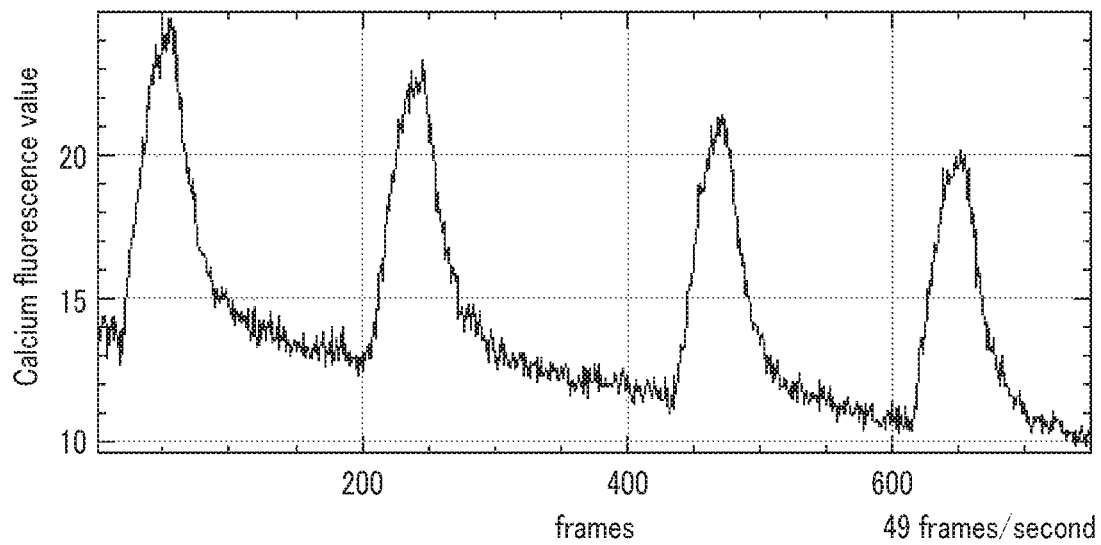
FIG. 6B is a waveform diagram of a sample 4D before addition of a drug.
Figure 6C:
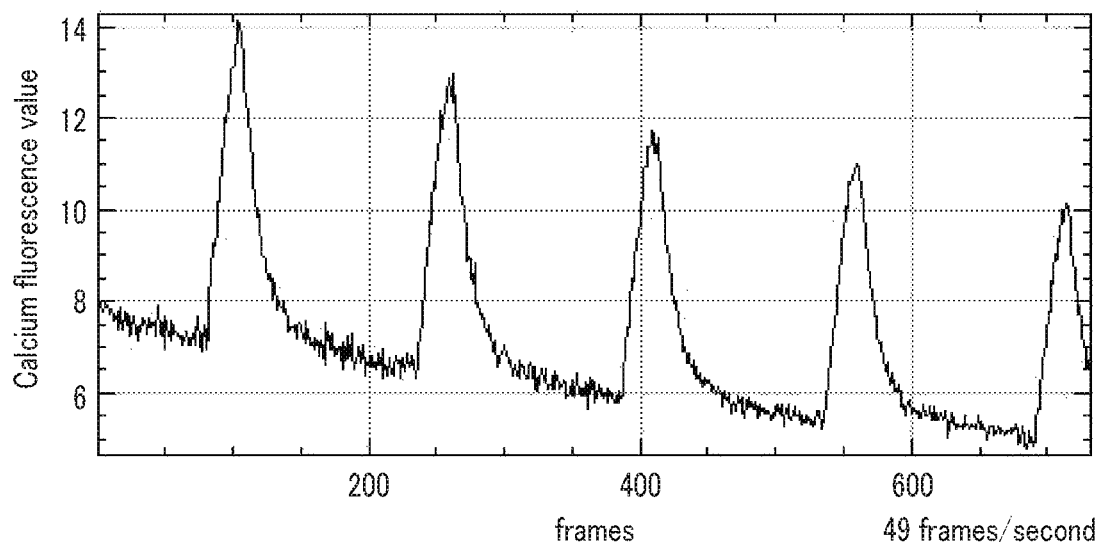
FIG. 6C is a waveform diagram of the sample 4D after addition of the drug.

When a cardiomyocyte sheet was placed in a culture medium contained in the oxygen-permeable container and 100 nM isoproterenol was added, an expected drug response was detected and the pulsation did not stop (sample 4C). Also, even when a cardiomyocyte sheet was placed in a culture medium contained in the oxygen-permeable container and 1000 nM isoproterenol was added, the pulsation stopped only at a low frequency (sample 4D). The results of sample 4D are shown in FIGS. 6B and 6C. FIG. 6B shows the waveform before the addition of the drug, and FIG. 6C shows the waveform after the addition of the drug.

Figure 7:
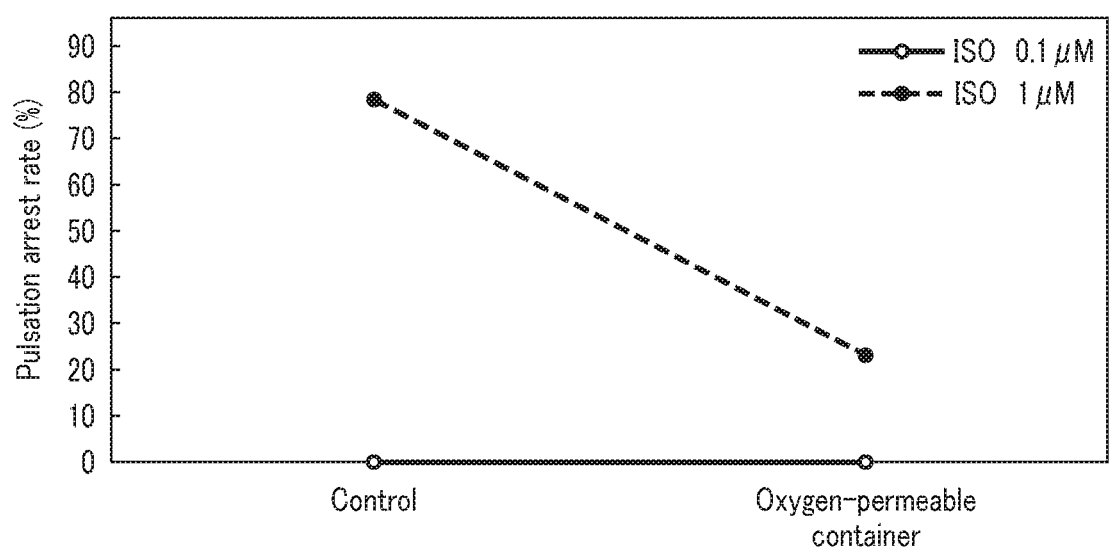
FIG. 7 is a graph showing a relationship between the type of a culture vessel and a pulsation arrest rate.

The results of samples 4A to 4D are shown together in FIG. 7. FIG. 7 shows the type of the culture vessel on the horizontal axis and the pulsation arrest rate on the vertical axis. FIG. 7 shows that the occurrence of the pulsation arrest of the cardiomyocytes during the drug response testing can be suppressed by using the oxygen-permeable container. FIG. 7 also shows that the range of the drug concentration applicable in the drug response testing can be extended by using the oxygen-permeable container.

Example 5

In Example 5, drug response testing was conducted using drugs other than isoproterenol, that is, verapamil, E-4031, terfenadine, and milrinone.

[5-1] Drug Response Testing

Drug response testing was performed on the samples shown below according to the same procedure as in Example 1. In the same manner as in Example 1, cardiomyocytes were seeded at a cell number of $4 \times 10^4$ to $8 \times 10^4$ per well of a 96-well plate (i.e., $1.25 \times 10^5$ cells/cm$^2$ to $2.5 \times 10^5$ cells/cm$^2$) and cultured to produce beating cardiomyocyte sheets. The resulting cardiomyocyte sheets were used in the drug response testing.

TABLE 4

|  | Drug | Culture medium | Liquid-surface distance |
| --- | --- | --- | --- |
| Sample 5A | 0.1 μM Verapamil | Culture medium not containing hemoglobin | 6.67 mm |
| Sample 5B | 0.1 μM Verapamil | Culture medium containing 0.5 mass % of hemoglobin | 1.67 mm |
| Sample 5C | 0.3 μM Verapamil | Culture medium not containing hemoglobin | 6.67 mm |
| Sample 5D | 0.3 μM Verapamil | Culture medium containing 0.5 mass % of hemoglobin | 1.67 mm |
| Sample 5E | 0.1 μM E-4031 | Culture medium not containing hemoglobin | 6.67 mm |
| Sample 5F | 0.1 μM E-4031 | Culture medium containing 0.5 mass % of hemoglobin | 1.67 mm |

TABLE 4-continued

|  | Drug | Culture medium | Liquid-surface distance |
| --- | --- | --- | --- |
| Sample 5G | 0.3 μM E-4031 | Culture medium not containing hemoglobin | 6.67 mm |
| Sample 5H | 0.3 μM E-4031 | Culture medium containing 0.5 mass % of hemoglobin | 1.67 mm |
| Sample 5I | 0.1 μM Terfenadine | Culture medium not containing hemoglobin | 6.67 mm |
| Sample 5J | 0.1 μM Terfenadine | Culture medium containing 0.5 mass % of hemoglobin | 1.67 mm |
| Sample 5K | 0.7 μM Terfenadine | Culture medium not containing hemoglobin | 6.67 mm |
| Sample 5L | 0.7 μM Terfenadine | Culture medium containing 0.5 mass % of hemoglobin | 1.67 mm |
| Sample 5M | 300 μM Milrinone | Culture medium not containing hemoglobin | 6.67 mm |
| Sample 5N | 300 μM Milrinone | Culture medium containing 2.0 mass % of hemoglobin | 1.0 mm |
| Sample 5O | 500 μM Milrinone | Culture medium not containing hemoglobin | 6.67 mm |
| Sample 5P | 500 μM Milrinone | Culture medium containing 2.0 mass % of hemoglobin | 1.0 mm |

[5-2] Results of Verapamil

When a cardiomyocyte sheet was placed in a culture medium containing no hemoglobin and having a liquid-surface distance of 6.67 mm and 0.1 μM verapamil was added, an expected drug response (a decrease in the amplitude of the Ca$^{2+}$ waveform and bradycardic response) was detected, and the pulsation did not stop (sample 5A). When a cardiomyocyte sheet was placed in a culture medium containing 0.5% by mass of hemoglobin and having a liquid-surface distance of 1.67 mm and 0.1 μM verapamil was added, an expected drug response was detected, and the pulsation did not stop (sample 5B).

Figure 8A:
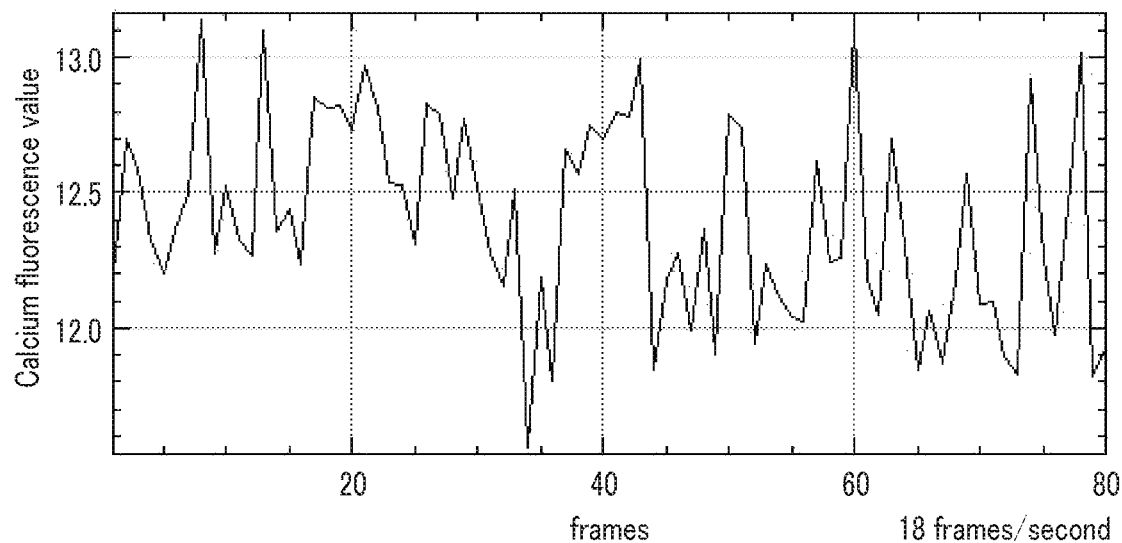
FIG. 8A is a waveform diagram of a sample 5C after addition of a drug.
Figure 8B:
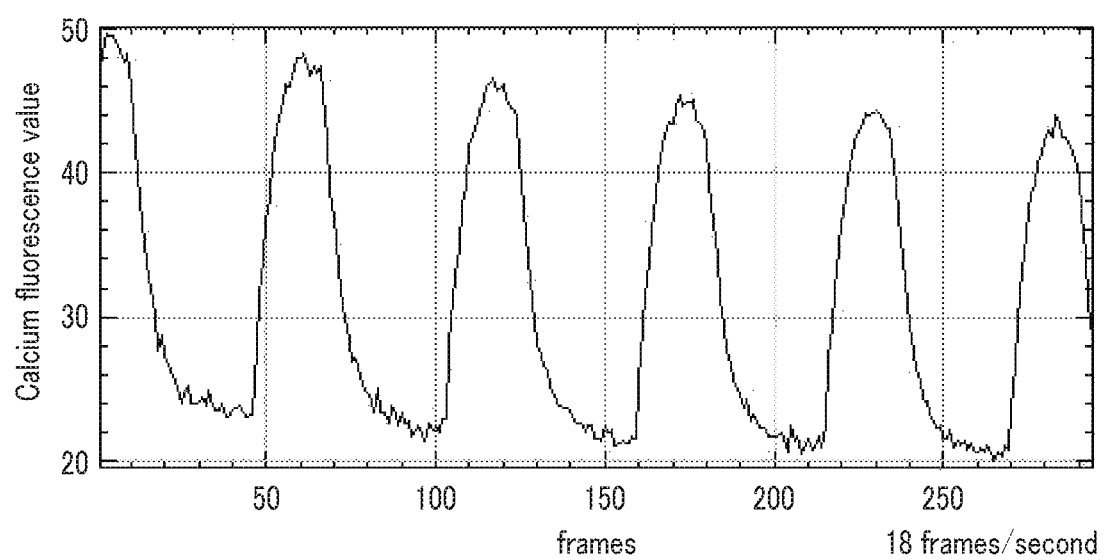
FIG. 8B is a waveform diagram of a sample 5D before addition of a drug.
Figure 8C:
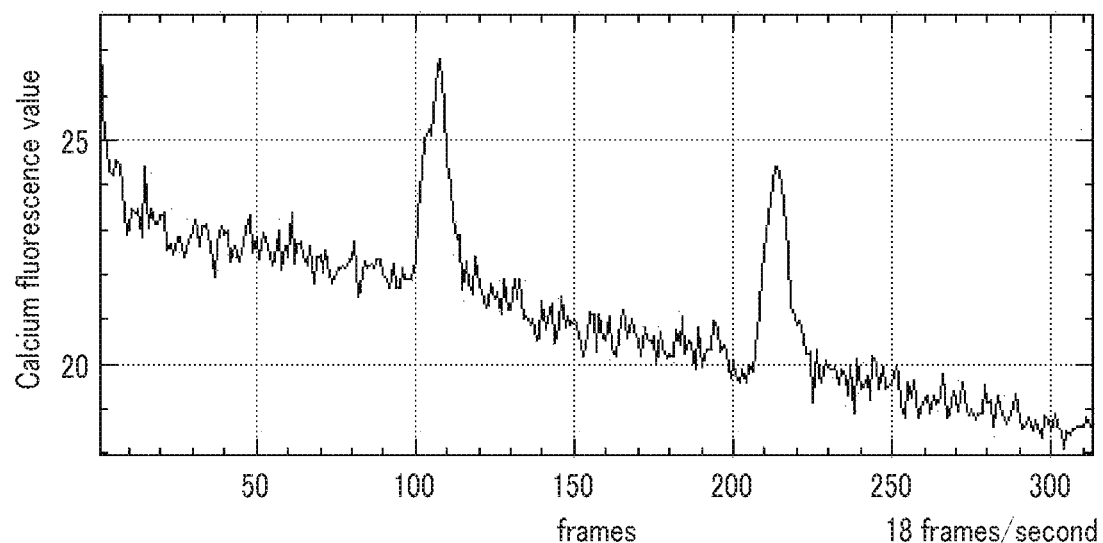
FIG. 8C is a waveform diagram of the sample 5D after addition of the drug.

When a cardiomyocyte sheet was placed in a culture medium containing no hemoglobin and having a liquid-surface distance of 6.67 mm and 0.3 μM verapamil was added, the pulsation stopped at a high frequency (sample 5C). The results of sample 5C are shown in FIG. 8A. FIG. 8A shows the waveform after the addition of the drug. On the other hand, when a cardiomyocyte sheet was placed in a culture medium containing 0.5% by mass of hemoglobin and having a liquid-surface distance of 1.67 mm and 0.3 μM verapamil was added, an expected drug response was detected and the pulsation did not stop (sample 5D). The results of sample 5D are shown in FIGS. 8B and 8C. FIG. 8B shows the waveform before the addition of the drug, and FIG. 8C shows the waveform after the addition of the drug.

Figure 9:
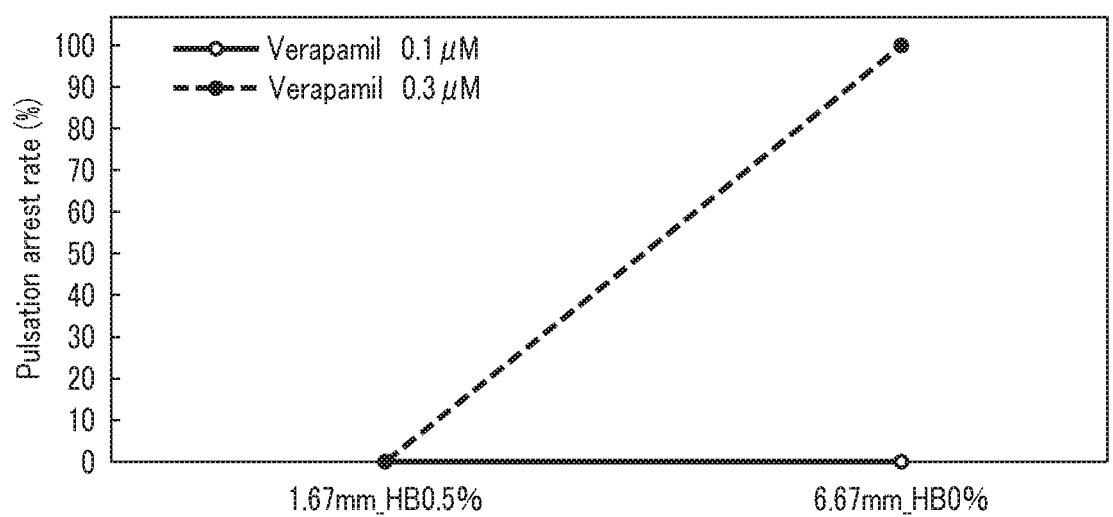
FIG. 9 is a graph showing a relationship between the conditions of drug response testing and a pulsation arrest rate.

The results of samples 5A to 5D are shown together in FIG. 9. FIG. 9 shows the conditions of the drug response testing (i.e., the liquid-surface distance and the hemoglobin concentration) on the horizontal axis and the pulsation arrest rate on the vertical axis. FIG. 9 shows that, in the case of verapamil as well, the occurrence of the pulsation arrest of the cardiomyocytes during the drug response testing can be suppressed when hemoglobin is added to the culture medium and the liquid-surface distance is shortened. FIG. 9 also shows that, in the case of verapamil as well, the range of the drug concentration applicable in the drug response testing can be extended when hemoglobin is added to the culture medium and the liquid-surface distance is shortened.

[5-3] Results of E-4031

When a cardiomyocyte sheet was placed in a culture medium containing no hemoglobin and having a liquid-surface distance of 6.67 mm and 0.1 µM E-4031 was added, an expected drug response (prolongation of the duration of the $Ca^{2+}$ waveform or EAD arrhythmia) was detected and the pulsation did not stop (sample 5E). When a cardiomyocyte sheet was placed in a culture medium containing 0.5% by mass of hemoglobin and having a liquid-surface distance of 1.67 mm and 0.1 µM E-4031 was added, an expected drug response was detected and the pulsation did not stop (sample 5F).

Figure 10A:
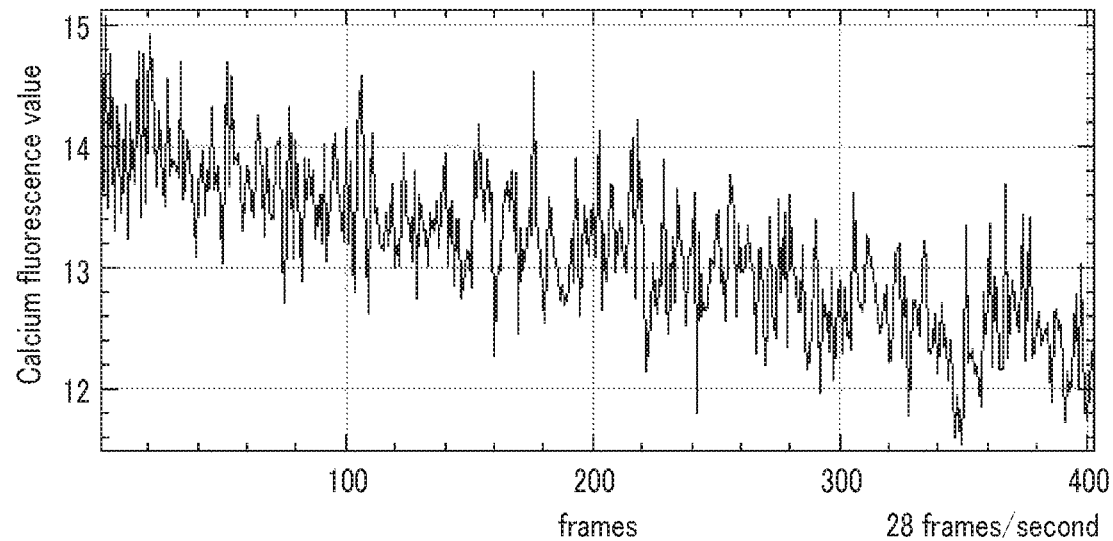
FIG. 10A is a waveform diagram of a sample 5G after addition of a drug.
Figure 10B:
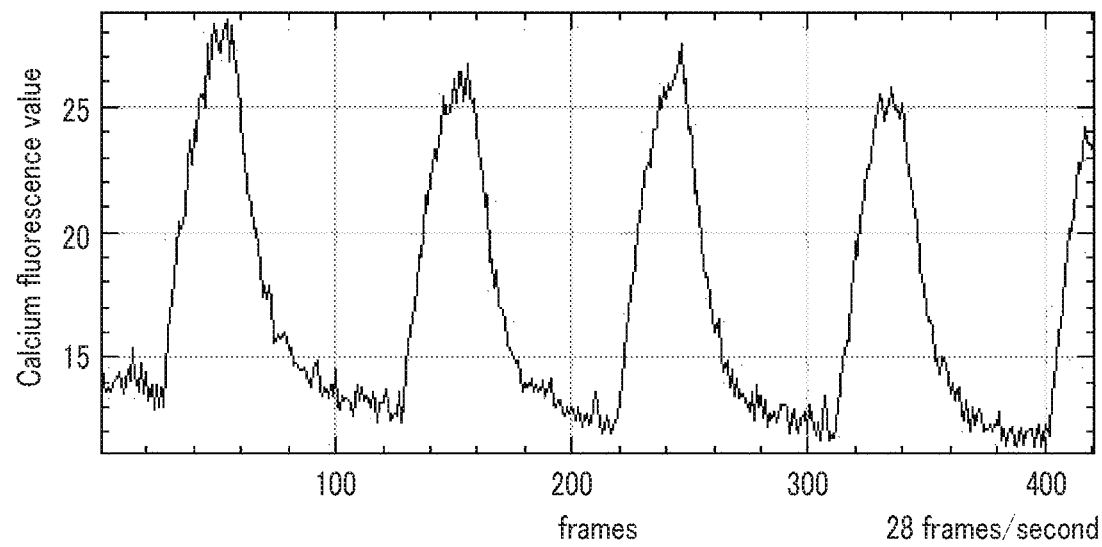
FIG. 10B is a waveform diagram of a sample 5H before addition of a drug.
Figure 10C:
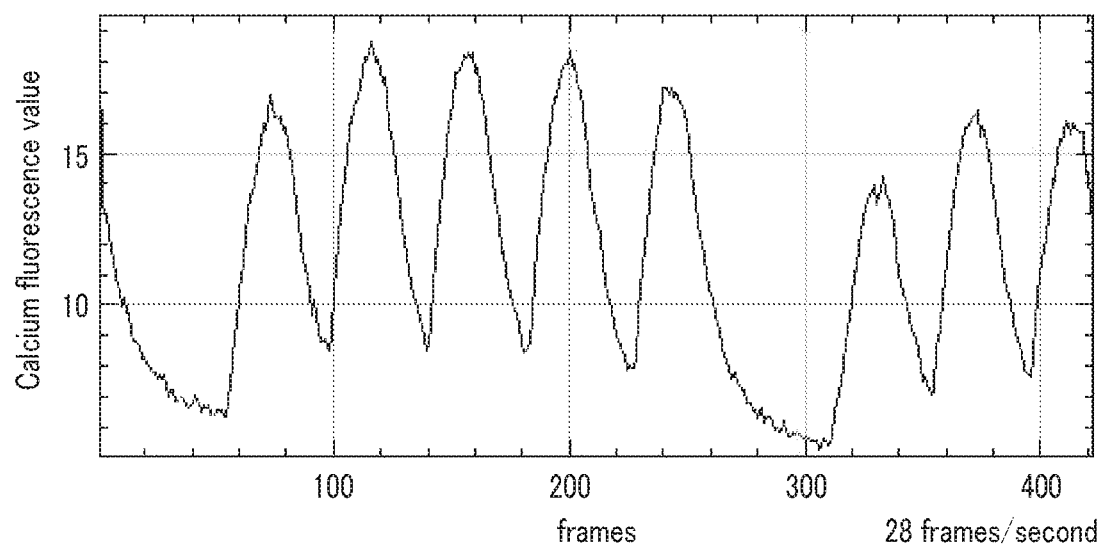
FIG. 10C is a waveform diagram of the sample 5H after addition of the drug.

When a cardiomyocyte sheet was placed in a culture medium containing no hemoglobin and having a liquid-surface distance of 6.67 mm and 0.3 µM E-4031 was added, the pulsation stopped at a high frequency (sample 5G). The results of sample 5G are shown in FIG. 10A. FIG. 10A shows the waveform after the addition of the drug. On the other hand, when a cardiomyocyte sheet was placed in a culture medium containing 0.5% by mass of hemoglobin and having a liquid-surface distance of 1.67 mm and 0.3 µM E-4031 was added, an expected drug response (EAD arrhythmia) was detected and the pulsation did not stop (sample 5H). The results of sample 5H are shown in FIGS. 10B and 10C. FIG. 10B shows the waveform before the addition of the drug, and FIG. 10C shows the waveform (EAD arrhythmia response) after the addition of the drug.

Figure 11:
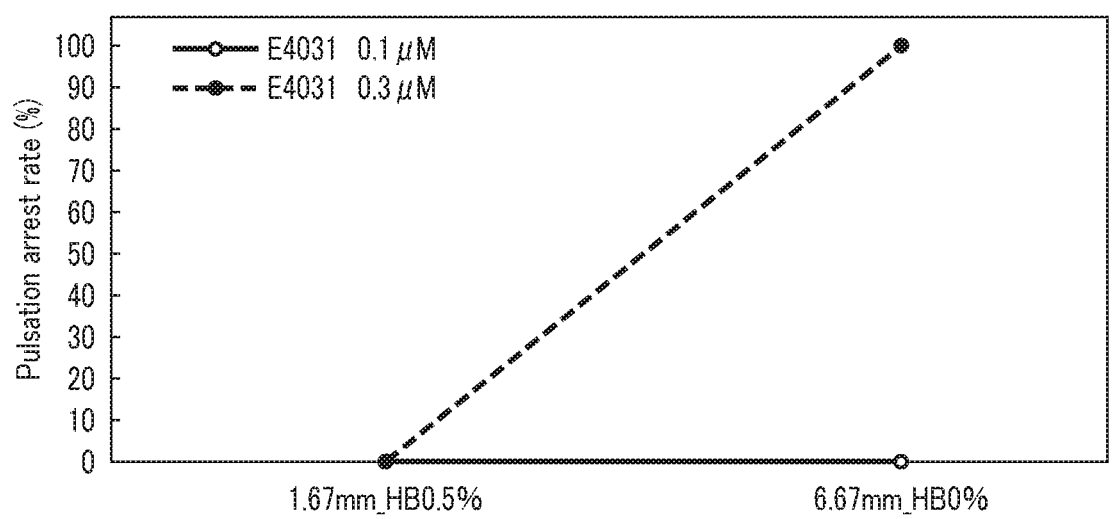
FIG. 11 is a graph showing a relationship between the conditions of drug response testing and a pulsation arrest rate.

The results of samples 5E to 5H are shown together in FIG. 11. FIG. 11 shows the conditions of the drug response testing (i.e., the liquid-surface distance and the hemoglobin concentration) on the horizontal axis and the pulsation arrest rate on the vertical axis. FIG. 11 shows that, in the case of E-4031 as well, the occurrence of the pulsation arrest of the cardiomyocytes during the drug response testing can be suppressed when hemoglobin is added to the culture medium and the liquid-surface distance is shortened. FIG. 11 also shows that, in the case of E-4031 as well, the range of the drug concentration applicable in the drug response testing can be extended when hemoglobin is added to the culture medium and the liquid-surface distance is shortened.

[5-4] Results of Terfenadine

When a cardiomyocyte sheet was placed in a culture medium containing no hemoglobin and having a liquid-surface distance of 6.67 mm and 0.1 µM terfenadine was added, an expected drug response (QT prolongation) was detected and the pulsation did not stop (sample 5I). When a cardiomyocyte sheet was placed in a culture medium containing 0.5% by mass of hemoglobin and having a liquid-surface distance of 1.67 mm and 0.1 µM terfenadine was added, an expected drug response was detected and the pulsation did not stop (sample 5J).

Figure 12C:
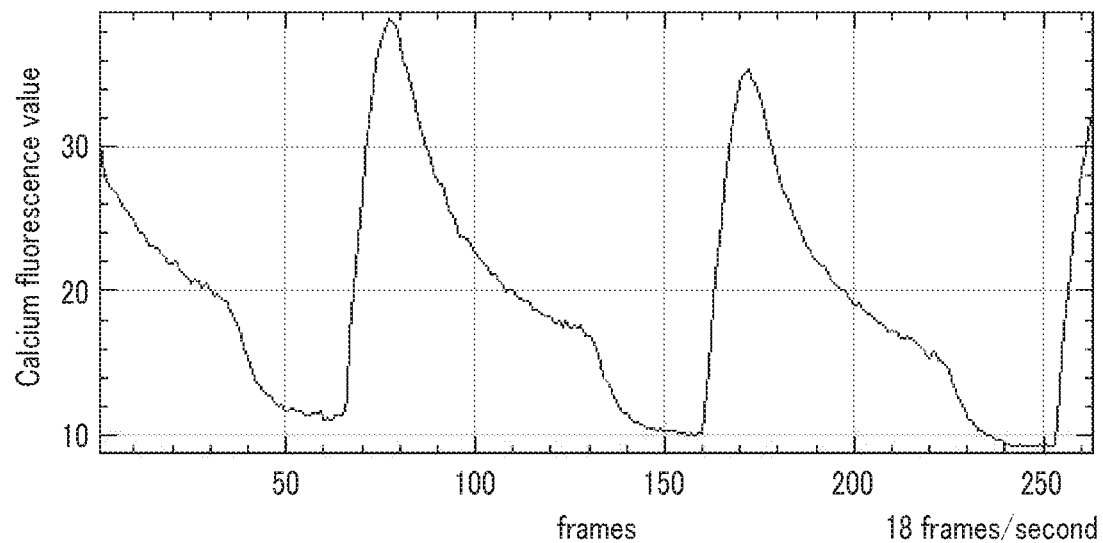
FIG. 12C is a waveform diagram of the sample 5L after addition of the drug.

When a cardiomyocyte sheet was placed in a culture medium containing no hemoglobin and having a liquid-surface distance of 6.67 mm and 0.7 µM terfenadine was added, the pulsation stopped at a high frequency (sample 5K). The results of sample 5K are shown in FIG. 12A. FIG. 12A shows the waveform after the addition of the drug. On the other hand, when a cardiomyocyte sheet was placed in a culture medium containing 0.5% by mass of hemoglobin and having a liquid-surface distance of 1.67 mm and 0.7 µM terfenadine was added, an expected drug response (prolongation of the duration of the $Ca^{2+}$ waveform) was detected and the pulsation did not stop (sample 5L). The results of sample 5L are shown in FIGS. 12B and 12C. FIG. 12B shows the waveform before the addition of the drug, and FIG. 12C shows the waveform after the addition of the drug.

Figure 13:
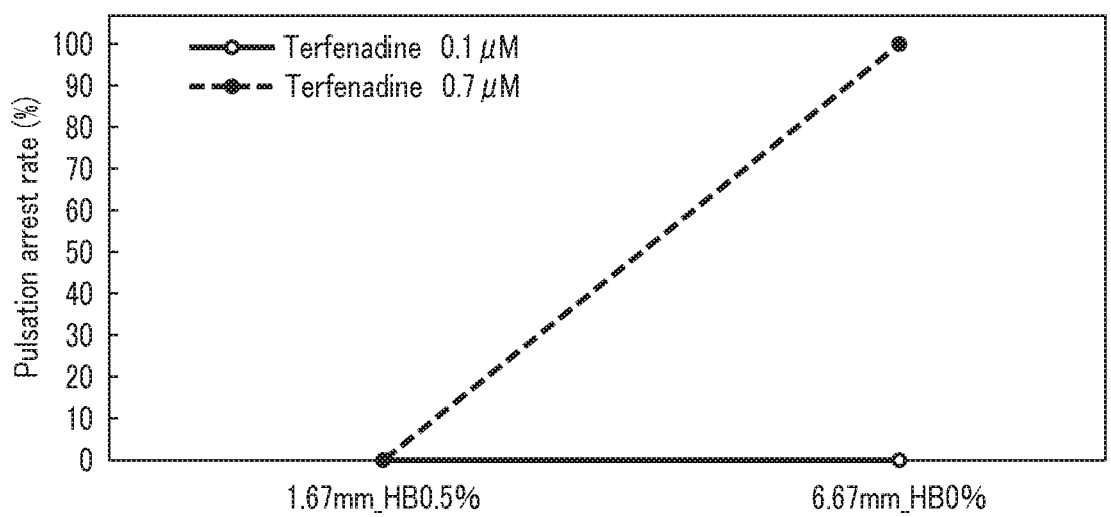
FIG. 13 is a graph showing a relationship between the conditions of drug response testing and a pulsation arrest rate.

The results of samples 5I to 5L are shown together in FIG. 13. FIG. 13 shows the conditions of the drug response testing (i.e., the liquid-surface distance and the hemoglobin concentration) on the horizontal axis and the pulsation arrest rate on the vertical axis. FIG. 13 shows that, in the case of terfenadine as well, the occurrence of the pulsation arrest of the cardiomyocytes during the drug response testing can be suppressed when hemoglobin is added to the culture medium and the liquid-surface distance is shortened. FIG. 13 also shows that, in the case of terfenadine as well, the range of the drug concentration applicable in the drug response testing can be extended when hemoglobin is added to the culture medium and the liquid-surface distance is shortened.

[5-5] Results of Milrinone

A "rate of change in heart rate" was determined as follows:

Rate of change in heart rate (%)=(heart rate after addition of drug/heart rate before addition of drug)×100.

The heart rate was determined based on the number of waves of the $Ca^{2+}$ waveform per minute.

The rate of change is represented by 100% when no change is observed, and the rate of change takes a value of 100% or greater when tachycardia occurs.

When a cardiomyocyte sheet was placed in a culture medium containing no hemoglobin and having a liquid-surface distance of 6.67 mm and 300 µM milrinone was added, an expected drug response (tachycardic response) was not detected (rate of change in heart rate: 79%), and the pulsation did not stop (sample 5M). When a cardiomyocyte sheet was placed in a culture medium containing 2.0% by mass of hemoglobin and having a liquid-surface distance of 1.0 mm and 300 µM milrinone was added, an expected drug response was detected (rate of change in heart rate: 118%), and the pulsation did not stop (sample 5N).

Figure 14C:
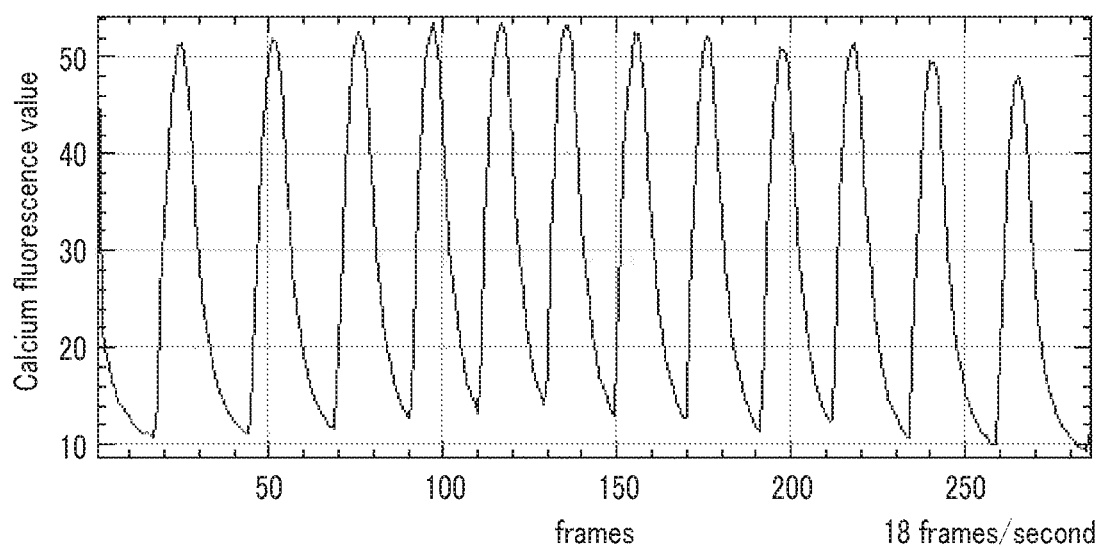
FIG. 14C is a waveform diagram of the sample 5P after addition of the drug.

When a cardiomyocyte sheet was placed in a culture medium containing no hemoglobin and having a liquid-surface distance of 6.67 mm and 500 µM milrinone was added, the pulsation stopped at a high frequency (sample 5O). The results of sample 5O are shown in FIG. 14A. FIG. 14A shows the waveform after the addition of the drug. On the other hand, when a cardiomyocyte sheet was placed in a culture medium containing 2.0% by mass of hemoglobin and having a liquid-surface distance of 1.0 mm and 500 µM milrinone was added, an expected drug response (tachycardic response) was detected (rate of change in heart rate: 154%), and the pulsation did not stop (sample 5P). The results of sample 5P are shown in FIGS. 14B and 14C. FIG. 14B shows the waveform before the addition of the drug, and FIG. 14C shows the waveform after the addition of the drug.

The above results show that, in the case of milrinone as well, the occurrence of the pulsation arrest of the cardiomyocytes during the drug response testing can be suppressed when hemoglobin is added to the culture medium at a higher concentration and the liquid-surface distance is further shortened. The above results also show that the tachycardic response caused by milrinone, which has conventionally been difficult to detect in iPS cell-derived cardiomyocytes, can be detected.

Example 6

In Example 6, drug response testing was performed using terfenadine, and prolongation of the duration of the $Ca^{2+}$ waveform, which corresponds to QT prolongation, and EAD arrhythmia were evaluated.

[6-1] Drug Response Testing

Drug response testing was performed on the samples shown below according to the same procedure as in Example 1. In the same manner as in Example 1, cardiomyocytes were seeded at a cell number of $4\times10^4$ to $8\times10^4$ per well of a 96-well plate (i.e., $1.25\times10^5$ cells/cm$^2$ to $2.5\times10^5$ cells/cm$^2$) and cultured to produce beating cardiomyocyte sheets. The resulting cardiomyocyte sheets were used in the drug response testing.

TABLE 5

| | Drug | Culture medium | Liquid-surface distance |
|---|---|---|---|
| Sample 6A | 0.3 µM Terfenadine | Culture medium containing 0.5 mass % of hemoglobin | 1.67 mm |
| Sample 6B | 0.5 µM Terfenadine | Culture medium containing 0.5 mass % of hemoglobin | 1.67 mm |
| Sample 6C | 0.9 µM Terfenadine | Culture medium containing 0.5 mass % of hemoglobin | 1.67 mm |
| Sample 6D | 1.5 µM Terfenadine | Culture medium containing 0.5 mass % of hemoglobin | 1.67 mm |
| Sample 6E | 0.7 µM Terfenadine | Culture medium containing 2.0 mass % of hemoglobin | 1.0 mm |
| Sample 6F | 0.9 µM Terfenadine | Culture medium containing 2.0 mass % of hemoglobin | 1.0 mm |
| Sample 6G | 1.5 µM Terfenadine | Culture medium containing 2.0 mass % of hemoglobin | 1.0 mm |
| Sample 6H | 0.9 µM Terfenadine | Culture medium containing 2.0 mass % of hemoglobin | 1.0 mm |
| Sample 6I | 1.5 µM Terfenadine | Culture medium containing 2.0 mass % of hemoglobin | 1.0 mm |

A duration ($T_B$) from the time when the $Ca^{2+}$ waveform rises before the addition of the drug and a duration ($T_A$) from the time when the $Ca^{2+}$ waveform rises after the addition of the drug were measured, and a "rate of change in the $Ca^{2+}$ duration" was determined based on the measured values by the following equation:

$$\text{Rate of change in } Ca^{2+} \text{ duration (\%)} = (T_A/T_B)\times 100$$

When no change is observed, the rate of change is given as 100%.

Also, in regard to an "EAD incidence rate", a waveform in which a calcium fluorescence value increased and returned to a baseline was regarded as one $Ca^{2+}$ waveform, a waveform in which two or more peaks were successively generated in one $Ca^{2+}$ waveform was regarded as EAD, and the case where one or more $Ca^{2+}$ waveforms corresponding to EAD were observed was regarded as a "cardiomyocyte sheet in which EAD occurred".

$$\text{EAD incidence rate (\%)} = (\text{Number of cardiomyocyte sheets in which EAD occurred/Number of cardiomyocyte sheets in which EAD did not occur})\times 100$$

[6-2] Results

Figure 15A:
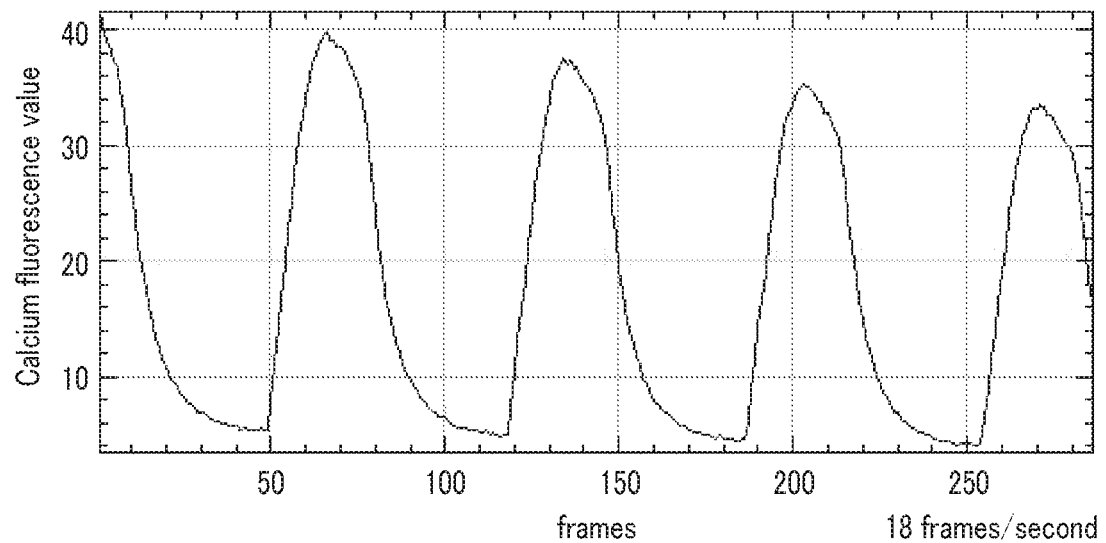
FIG. 15A is a waveform diagram of a sample 6B before addition of a drug.
Figure 15B:
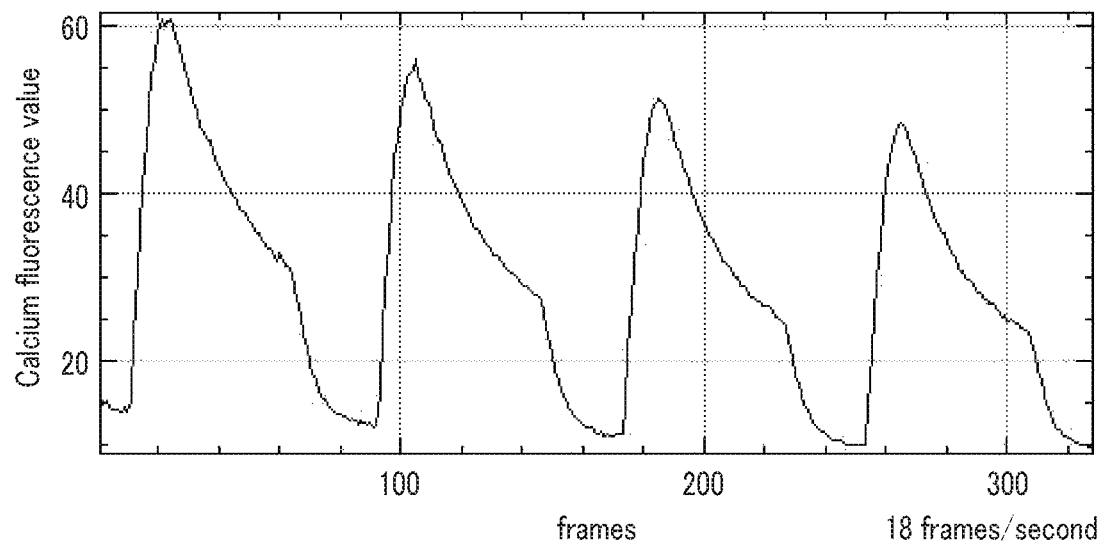
FIG. 15B is a waveform diagram of the sample 6B after addition of the drug.

When a cardiomyocyte sheet was placed in a culture medium containing 0.5% by mass of hemoglobin and having a liquid-surface distance of 1.67 mm and 0.3 µM terfenadine was added, an expected drug response was detected in the form of a distinct change in the waveform (sample 6A). When a cardiomyocyte sheet was placed in a culture medium containing 0.5% by mass of hemoglobin and having a liquid-surface distance of 1.67 mm and 0.5 µM terfenadine was added, an expected drug response was detected in the form of a very distinct change in the waveform (sample 6B). The results of sample 6B are shown in FIGS. 15A and 15B. FIG. 15A shows the waveform before the addition of the drug, and FIG. 15B shows the waveform after the addition of the drug.

Figure 15C:
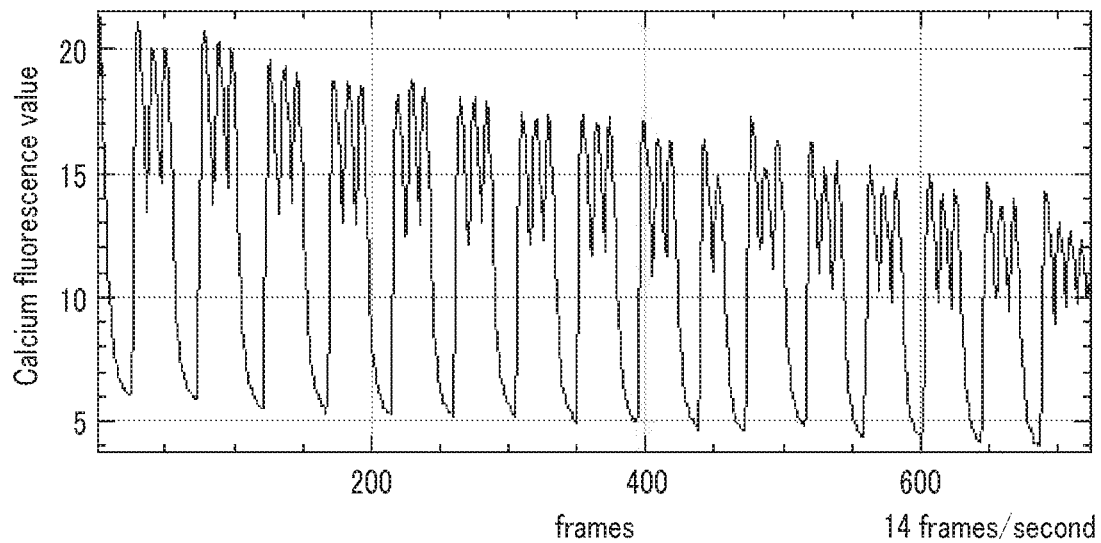
FIG. 15C is a waveform diagram of a sample 6F after addition of a drug.
Figure 15D:
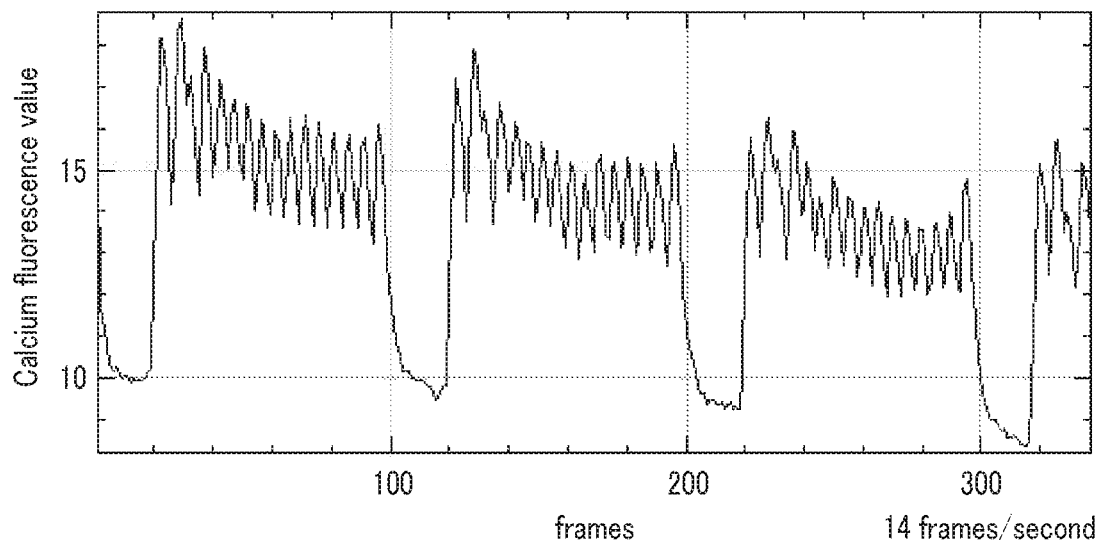
FIG. 15D is a waveform diagram of a sample 6G after addition of a drug.
Figure 15E:
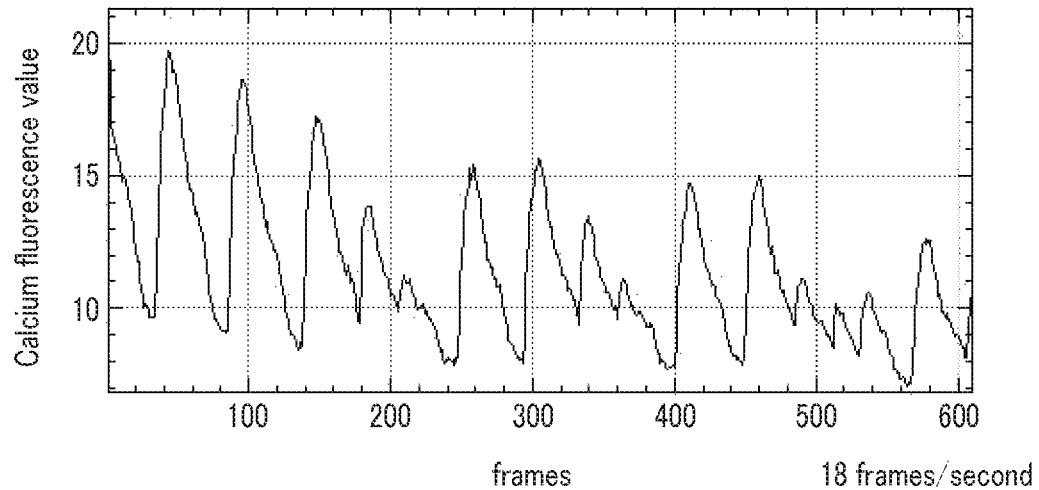
FIG. 15E is a waveform diagram of a sample 6H after addition of a drug.
Figure 15F:
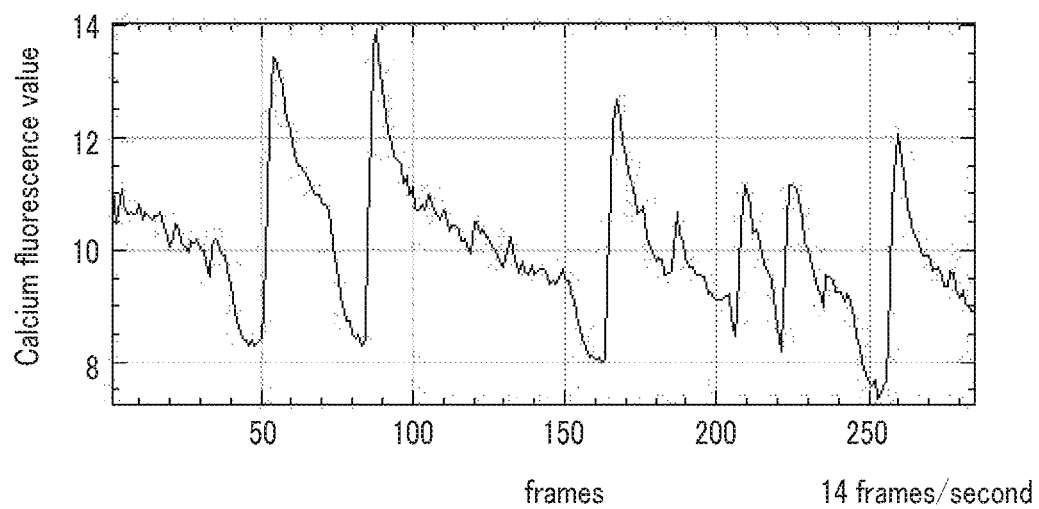
FIG. 15F is a waveform diagram of a sample 6I after addition of a drug.

When cardiomyocyte sheets were placed in culture media containing 0.5% by mass of hemoglobin and having a liquid-surface distance of 1.67 mm, and 0.7 µM terfenadine, 0.9 µM terfenadine, and 1.5 µM terfenadine were respectively added, prolongation of the duration of the $Ca^{2+}$ waveform, which was expected, was detected, but EAD was not detected (samples 5L, 6C, 6D). When cardiomyocyte sheets were placed in culture media containing 2.0% by mass of hemoglobin and having a liquid-surface distance of 1.0 mm, and 0.7 µM terfenadine, 0.9 µM terfenadine, and 1.5 µM terfenadine were respectively added, a distinct EAD was detected (samples 6E, 6F, 6G). The results of sample 6F are shown in FIG. 15C, and the results of sample 6G are shown in FIG. 15D. When cardiomyocyte sheets were placed in culture media containing 2.0% by mass of hemoglobin and having a liquid-surface distance of 1.0 mm, and 0.9 µM terfenadine and 1.5 µM terfenadine were respectively added, several torsades de pointes (TdP)-like waveforms, in which the amplitude and the peak interval of the waveform varied, were detected (samples 6H and 6I). The results of sample 6H are shown in FIG. 15E, and the results of sample 6I are shown in FIG. 15F.

Figure 16:
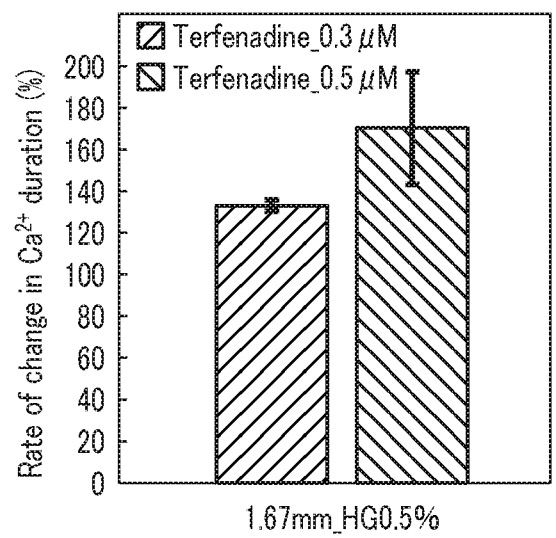
FIG. 16 is a graph showing a rate of change in $Ca^{2+}$ duration.

FIG. 16 shows the "rates of change in $Ca^{2+}$ duration" of samples 6A and 6B. The "rates of change in $Ca^{2+}$ duration" of samples 6A and 6B were about 135% and about 170%, respectively. FIG. 16 shows that when hemoglobin is added to the culture medium and the liquid-surface distance is shortened, the "rate of change in $Ca^{2+}$ duration" can be increased.

Figure 17:
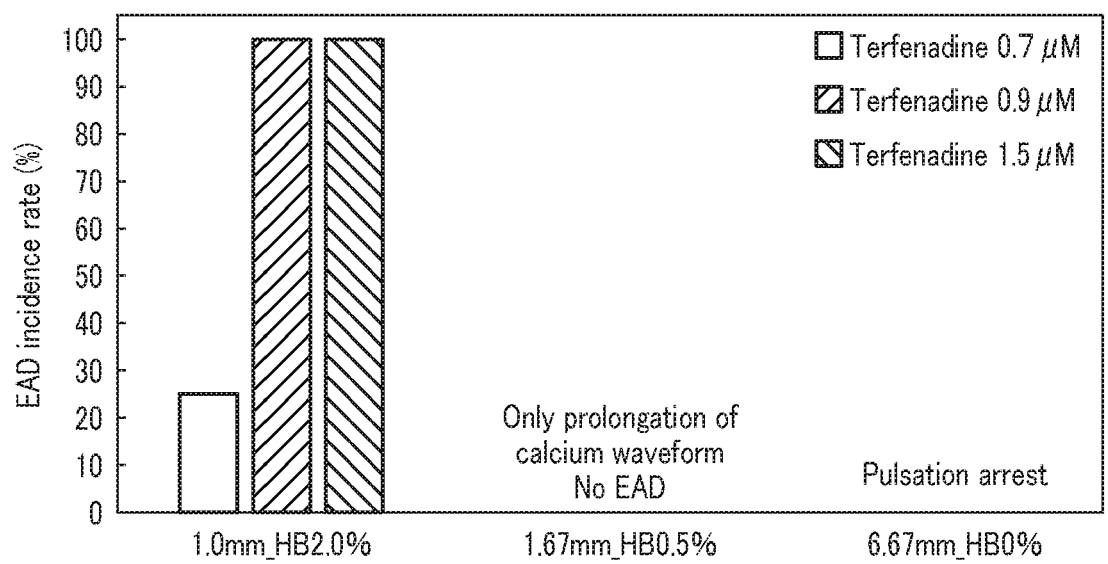
FIG. 17 is a graph showing an EAD incidence rate.

FIG. 17 shows the "EAD incidence rate" of the samples, including samples 6C to 6G. FIG. 17 shows the conditions of the drug response testing (i.e., the liquid-surface distance and the hemoglobin concentration) on the horizontal axis and the EAD incidence rate on the vertical axis. FIG. 17 shows that when hemoglobin is added to the culture medium at a higher concentration and the liquid-surface distance is further shortened, the "EAD incidence rate" can be increased. Also, the results of samples 6E to 6I show that EAD and TdP caused by terfenadine, which have conventionally been difficult to detect in iPS cell-derived cardiomyocytes, can be detected.

The results of the above examples show that the method of the present invention can not only detect various types of drug response caused by the addition of various drugs without stopping the pulsation of cardiomyocytes, but also detect changes in the waveform (such as tachycardic response, QT prolongation response, EAD response, TdP response, and the like) caused by the addition of drugs in the form of more distinct changes in the waveform. The "various types of drug response" described herein include drug-induced QT prolongation response, bradycardic response (negative chronotropic effect), tachycardic response (positive chronotropic effect), cardiotonic response (positive inotropic effect), cardiac weakening response (negative inotropic effect), early afterdepolarization (EAD) response, delayed afterdepolarization (DAD) response, torsades de pointes (TdP) response, triggered activity arrhythmia response, re-entry arrhythmia response, and the like, which are expected to be detected by the present invention. The term "cardiomyocyte" used herein includes a primary cultured cell isolated from the heart of an animal, a cardiomyocyte derived from a pluripotent stem cell (iCell of CDI, MiraCell of Takara Bio Inc., Cor.4U of Axiogenesis, etc.), and the like, and it is expected that the above-described drug response will be detected in these types of cardiomyocytes by the present invention.

Example 7

In Example 7, a relationship between a partial pressure of oxygen of a cardiomyocyte-containing culture medium and drug response was examined.

[7-1] Measurement of Partial Pressure of Oxygen

Cardiomyocyte-containing culture media (samples 7A to 7F) having different partial pressures of oxygen were prepared by varying the liquid-surface distance and the cell density as shown in Table 6. Specifically, cardiomyocytes were seeded in an exclusive 96-well plate accompanying the extracellular flux analyzer XFe96 (Agilent Technologies) at the cell densities shown in Table 6 and then cultured in a culture medium to produce cardiomyocyte sheets. The resulting cardiomyocyte sheets were placed in culture media having the liquid-surface distances shown in Table 6, respectively, to prepare cardiomyocyte-containing culture media (samples 7A to 7F). The same sample was prepared in triplicate using three wells. The cardiomyocyte sheets were present in the prepared cardiomyocyte-containing culture media in a state of being adhered to the bottom surface of the plate.

TABLE 6

| | Liquid-surface distance | Cell density | Partial pressure of oxygen |
|---|---|---|---|
| Sample 7A | 1.0 mm | $1.6 \times 10^5$ cells/cm$^2$ | 137 |
| Sample 7B | 2.0 mm | $1.6 \times 10^5$ cells/cm$^2$ | 136 |
| Sample 7C | 5.0 mm | $1.6 \times 10^5$ cells/cm$^2$ | 132 |
| Sample 7D | 10.0 mm | $1.6 \times 10^5$ cells/cm$^2$ | 122 |
| Sample 7E | 1.0 mm | $3.2 \times 10^5$ cells/cm$^2$ | 125 |
| Sample 7F | 10.0 mm | $3.2 \times 10^5$ cells/cm$^2$ | 98 |

Each of the cardiomyocyte-containing culture media was left to stand for about 0.5 hour, and then the partial pressure of oxygen of each of the cardiomyocyte-containing culture media was measured using the extracellular flux analyzer XFe96 (Agilent Technologies) to determine an average value (partial pressure of oxygen P1). The value of the partial pressure of oxygen P1 is shown in Table 6. Thereafter, each of the cardiomyocyte-containing culture media was further left to stand for 0.1 hour, and the partial pressures of oxygen of the culture media were measured using the extracellular flux analyzer XFe96 (Agilent Technologies) to determine an average value (partial pressure of oxygen P2).

In samples 7A, 7B, 7C and 7E, the cardiomyocyte-containing culture media had a partial pressure of oxygen of 125 mmHg or greater. Also, in all samples 7A to 7F, the value of the partial pressure of oxygen P2 was almost the same as the value of the partial pressure of oxygen P1. Thus, in samples 7A, 7B, 7C and 7E, it was confirmed that the cardiomyocyte-containing culture media were maintained to have a partial pressure of oxygen of 125 mmHg or greater. It was also confirmed that the partial pressure of oxygen did not substantially change due to the addition of the drugs used in the drug response testing.

It is understood from the above results that if it is confirmed that the partial pressure of oxygen shows a predetermined value of 125 mmHg or more at a representative point in time when the value of the partial pressure of oxygen is stable (i.e., about 0.5 hour after the cardiomyocyte-containing culture medium is prepared), the partial pressure of oxygen of the culture medium is maintained at a value that is almost the same as the predetermined value at other points in time as well by virtue of the environment in which the culture medium is replenished with oxygen from the atmosphere even if the cardiomyocytes consume oxygen in the culture medium.

[7-2] Drug Response Testing

Drug response testing was performed on samples 7A to 7F according to the same procedure as in Example 1. First, cardiomyocytes were seeded in a 96-well plate at the cell densities shown in Table 6 and then cultured in a culture medium to produce cardiomyocyte sheets. The resulting cardiomyocyte sheets were placed in culture media having the liquid-surface distances shown in Table 6, and the drug response testing was performed according to the same procedure as in Example 1. Terfenadine was used as a drug and added to the culture media to have a concentration of 1000 nM.

[7-3] Results

FIG. 18 shows the results of the measurement of the partial pressure of oxygen P1 and the results of the drug response testing.

In samples 7A, 7B, 7C and 7E, drug response (i.e., prolongation of the duration of the Ca$^{2+}$ waveform or EAD arrhythmia) caused by the addition of terfenadine was detected in the form of a distinct change in the waveform. As described above, the cardiomyocyte-containing culture media of these samples were maintained to have a partial pressure of oxygen of 125 mmHg or greater in the absence of terfenadine. It is considered that since the drug response testing was performed using the cardiomyocyte-containing culture media having a high partial pressure of oxygen in these samples, oxygen was promptly supplied to the culture media when the cardiomyocytes consumed oxygen in the culture media for metabolism and pulsation during the drug response testing, allowing the cardiomyocytes to properly exhibit the drug-response effect.

On the other hand, drug response (i.e., prolongation of the duration of the Ca$^{2+}$ waveform or EAD arrhythmia) caused by the addition of terfenadine was not detected in samples 7D and 7F. The cardiomyocyte-containing culture media of samples 7D and 7F had a partial pressure of oxygen of 122 mmHg and 98 mmHg, respectively, in the absence of terfenadine. It is considered that since the drug response testing was performed using the cardiomyocyte-containing culture media having a low partial pressure of oxygen in these samples, oxygen was not promptly supplied to the culture media when the cardiomyocytes consumed oxygen in the culture media for metabolism and pulsation during the drug response testing, preventing the cardiomyocytes from properly exhibiting the response effect to the addition of the drug.

Therefore, it is understood from the above results that the drug response testing of the cardiomyocytes can be stably performed if the drug response testing is performed under the condition in which the cardiomyocyte containing-culture media are maintained to have a partial pressure of oxygen of 125 mmHg or greater in the absence of the drug.

Example 8

In Example 8, testing of response of cardiomyocytes to a change in the pH of a culture medium was performed to examine the influence of the liquid-surface distance on the testing.

[8-1] Testing of Response to pH of Culture Medium

Testing of response of cardiomyocytes to the pH of a culture medium was performed on the samples shown below according to the same procedure as in Example 1. Cardiomyocytes were seeded in a 96-well plate at a cell density of $1.6 \times 10^5$ cells/cm$^2$ and cultured to produce beating cardiomyocyte sheets.

The resulting cardiomyocyte sheets were used to perform the testing in the following culture environment:

Sample 8A: culture medium having a pH of 7.2 and a liquid-surface distance of 1.0 mm Sample 8B: culture medium having a pH of 7.2 and a liquid-surface distance of 6.67 mm Sample 8C: culture medium having a pH of 7.6 and a liquid-surface distance of 1.0 mm Sample 8D: culture medium having a pH of 7.6 and a liquid-surface distance of 6.67 mm Sample 8E: culture medium having a pH of 8.0 and a liquid-surface distance of 1.0 mm Sample 8F: culture medium having a pH of 8.0 and a liquid-surface distance of 6.67 mm The pH of the culture media was adjusted by adding an NaOH solution.

[8-2] Results

The results are shown in FIG. 19. In FIG. 19, the vertical axis represents BPM (beats/minute). When the liquid-surface distance was 1.0 mm, the BPM tended to increase as the pH was increased. That is, a tachycardic response due to a high pH was observed, as is known to be a common nature of cardiomyocytes. On the other hand, when the liquid-surface distance was 6.67 mm, there was no apparent increase in the BPM due to a high pH, and the pulsation stopped at a pH of 8.0.

It was found from the above results that the response of the cardiomyocytes to the change in the pH of the culture media was also easier to detect by shortening the liquid-surface distance, as in the case of the response of the cardiomyocytes to the drug (Example 3). It is considered that shortening the liquid-surface distance reduced the distance between the cardiomyocytes in contact with the bottom surface of the culture vessel and the atmosphere and increased the rate of oxygen supply to the cardiomyocytes, allowing the cardiomyocytes to properly exhibit the response effect to the changes in the culture environment such as a change in the pH of the culture media and the like.

The invention claimed is:

1. A method for testing drug response of cardiomyocytes, the method comprising:
    (a) testing a response of the cardiomyocytes to an added drug in a culture medium under a condition in which a distance from a liquid surface of the culture medium to a bottom surface of a culture vessel contacted by the cardiomyocytes is 5.0 mm or less; or
    (b) testing a response of the cardiomyocytes to an added drug immediately after placing the cardiomyocytes in a culture medium under a condition in which a distance from a liquid surface of the culture medium to a bottom surface of a culture vessel contacted by the cardiomyocytes is 5.0 mm or less, wherein
    (i) the cell density of the cardiomyocytes in the culture medium is greater than or equal to $2.5 \times 10^5$ cells/cm$^2$, and the distance from the liquid surface of the culture medium to the bottom surface of the culture vessel is 1.5 mm or less; or
    (ii) the cell density of the cardiomyocytes in the culture medium is equal to or greater than $1.25 \times 10^5$ cells/cm$^2$, and less than $2.5 \times 10^5$ cells/cm$^2$, and the distance from the liquid surface of the culture medium to the bottom surface of the culture vessel contacted by the cardiomyocyte is 3.5 mm or less; or
    (iii) the cell density of the cardiomyocytes in the culture medium is greater than or equal to $0.625 \times 10^5$ cells/cm$^2$ and less than $1.25 \times 10^5$ cells/cm$^2$, and the distance from the liquid surface of the culture medium to the bottom surface of the culture vessel is 5.0 mm or less.

2. The method according to claim 1, wherein the method comprises:
    testing a response of the cardiomyocyte to an added drug in a culture medium under a condition in which a distance from a liquid surface of the culture medium to a bottom surface of a culture vessel contacted by the cardiomyocyte is 5.0 mm or less.

3. The method according to claim 1, wherein the culture medium is a culture medium containing an oxygen carrier.

4. The method according to claim 2, wherein the culture medium is a culture medium containing an oxygen carrier.

5. The method according to claim 1, wherein the culture medium is contained in a container having an oxygen permeability.

* * * * *